United States Patent
Kelley

(10) Patent No.: US 11,456,055 B2
(45) Date of Patent: Sep. 27, 2022

(54) GENOTYPING POLYPLOID LOCI

(71) Applicant: Illumina, Inc., San Diego, CA (US)

(72) Inventor: Ryan Kelley, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 864 days.

(21) Appl. No.: 16/305,818

(22) PCT Filed: Jun. 2, 2017

(86) PCT No.: PCT/US2017/035751
§ 371 (c)(1),
(2) Date: Nov. 29, 2018

(87) PCT Pub. No.: WO2017/210603
PCT Pub. Date: Dec. 7, 2017

(65) Prior Publication Data
US 2020/0321075 A1      Oct. 8, 2020

Related U.S. Application Data

(60) Provisional application No. 62/345,577, filed on Jun. 3, 2016.

(51) Int. Cl.
*G16B 20/20* (2019.01)
*G16B 40/30* (2019.01)
*G16B 5/20* (2019.01)
*G16B 40/20* (2019.01)

(52) U.S. Cl.
CPC .............. *G16B 20/20* (2019.02); *G16B 5/20* (2019.02); *G16B 40/20* (2019.02); *G16B 40/30* (2019.02)

(58) Field of Classification Search
CPC .......... G16B 20/20; G16B 5/20; G16B 40/20; G16B 40/30; G16B 40/00; G16B 20/00; G16B 99/00; G16B 5/00
See application file for complete search history.

(56) References Cited

U.S. PATENT DOCUMENTS

| | | | |
|---|---|---|---|
| 2010/0221708 A1* | 9/2010 | Yamada | C12Q 1/6841 435/6.14 |
| 2011/0288780 A1* | 11/2011 | Rabinowitz | C12Q 1/6869 702/19 |
| 2016/0371432 A1* | 12/2016 | Rabinowitz | G16B 20/00 |

(Continued)

OTHER PUBLICATIONS

Serang, Oliver, Marcelo Mollinari, and Antonio Augusto Franco Garcia. "Efficient exact maximum a posteriori computation for Bayesian SNP genotyping in polyploids." PLoS One 7, No. 2 (2012): e30906. (Year: 2012).*

(Continued)

*Primary Examiner* — Jesse P Frumkin
(74) *Attorney, Agent, or Firm* — Weaver Austin Villeneuve & Sampson LLP

(57) ABSTRACT

Provided are methods, systems, and computer products for genotyping polyploid organisms, as well as diploid organisms. The provided methods use an allele-intensity model to generate cluster definitions. The allele-intensity model relates allele counts of different genotypes to signal intensities generated by the genotyping platform. The model also includes a capability to update cluster positions obtained from a maximum likelihood model using a Bayesian method.

20 Claims, 13 Drawing Sheets

(56) References Cited

U.S. PATENT DOCUMENTS

2018/0148777 A1* 5/2018 Kirkizlar .............. C12Q 1/6858

OTHER PUBLICATIONS

Dufresne, France, Marc Stiff, Roland Vergilino, and Barbara K. Mable. "Recent progress and challenges in population genetics of polyploid organisms: an overview of current state-of-the-art molecular and statistical tools." Molecular ecology 23, No. 1 (2014): 40-69. (Year: 2014).*

International Search Report and Written Opinion dated Sep. 11, 2018 issued in Application No. PCT/US2017/035751.

Akhunov et al., "Single nucleotide polymorphism genotyping in polyploid wheat with the Illumina GoldenGate assay," Theor Appl Genet (2009) 119:507-517 DOI 10.1007/s00122-009-1059-5, May 2009.

Bassil et al., "Development and preliminary evaluation of a 90 K Axiom® SNP array for the allo-octoploid cultivated strawberry Fragaria × ananassa," BMC Genomics (2015) 16:15 DOI 10.1186/s12864-015-1310-1, 2015.

Voorrips et al: "Genotype calling in tetrapioid species from bi-allelic marker data using mixture models", BMC Bioinformatics, Biomed Central, London, GB, vol. 12, No. 1, May 19, 2011.

Xie et al: "Statistical methods of background correction for Illumina BeadArray data", Bioi Nformati Cs, vol. 25, No. 6, Mar. 15, 2009.

International Preliminary Report on Patentability dated Dec. 13, 2018 issued in PCT Application No. PCT/US2017/035751.

EP Office Action dated Jun. 2, 2022, in Application No. EP17729717.3.

* cited by examiner

GENOTYPING POLYPLOID LOCI

CROSS REFERENCE TO RELATED APPLICATIONS

This application is a national phase application of and claims benefit and priority to International Patent Application No. PCT/US2017/035751 under 35 U.S.C. § 371, filed Jun. 2, 2017; which claims benefits and priority to U.S. Provisional Patent Application No. 62/345,577, filed Jun. 3, 2016; all of the above prior applications are herein incorporated by reference in their entireties for all purposes.

BACKGROUND

The disclosure relates to technology for genotyping various organisms. More specifically, the disclosure relates to systems and methods for using cluster models to genotype polyploid organisms.

In various applications involving, e.g., microarray data, a genotyping process provides signals such as fluorescence intensities for alleles. The genotypes are assigned by comparing the relative strengths of these intensities for different alleles. One method for assigning a genotype to a sample is to define data clusters for different genotypes, and assign the genotype of the cluster to the sample if the sample belongs to a cluster. Some methods generate clusters for diploid organisms, but have various limitations, especially with regard to polyploid organisms.

SUMMARY

One aspect of the disclosure provides various methods for genotyping polyploid organisms. In one implementation, a method is provided for producing a cluster model for genotyping polyploid organisms. The method including: (a) identifying a plurality of active genotypes expected to be observed at a genomic locus in the polyploid organisms; (b) fitting a plurality of parameters of a first function relating a first signal magnitude produced in a microarray by a first nucleotide type present in a first allele at the genomic locus to a count of the first nucleotide type at the genomic locus, wherein fitting the plurality of parameters of the first function assumes the identified plurality of active genotypes are observed in the polyploid organisms; (c) fitting a plurality of parameters of a second function relating a second signal magnitude produced in the microarray by a second nucleotide type present in a second allele at the genomic locus to a count of the second nucleotide type at the genomic locus, wherein fitting the plurality of parameters of the second function assumes the identified plurality of active genotypes are observed in the polyploid organisms, wherein fitting the plurality of parameters to the first and second functions is performed using a training set of the first and second signal magnitudes obtained by assaying the genomic locus of a plurality of polyploid organisms, and wherein the first and second functions together identify cluster positions for genotypes at the genomic locus; and (d) adjusting the cluster positions identified by the first and second functions to more closely match observed data from the training set.

In some implementations, identifying the plurality of active genotypes includes identifying fewer than all possible combinations of the first and second nucleotide types at the genomic locus.

In some implementations, the polyploid genome is an allopolyploid genome. In some implementations, the polyploid genome is an allotetraploid genome and at most three active genotypes are identified.

In some implementations, at least one of the first and second functions of the cluster model has the form:

$$\text{intensity}_a = x^*(\text{counts}_{\text{allele } a})^y + z$$

wherein x, y, and z are adjustable parameters, $\text{intensity}_a$ is the first signal magnitude produced in the microarray, and $\text{counts}_{\text{allele } a}$ is the count of the first nucleotide type at the genomic locus. In some implementations, both the first and second function has the form above. In some implementations, at least one of the first and second functions is a non-linear function.

In some implementations, fitting a plurality of parameters of the first and second functions in (b) and (c) includes an unsupervised machine learning process. In some implementations, fitting a plurality of parameters of the first and second functions in (b) and (c) includes a supervised machine learning process. In some implementations, fitting a plurality of parameters of at least one the first and second functions in (b) and (c) includes a gradient method. In some implementations, the gradient method is a maximum likelihood estimation. In some implementations, the maximum likelihood estimation fits the adjustable parameters to the training set data using a Gaussian definition of clusters in the training set. In some implementations, the maximum likelihood estimation fits the adjustable parameters to the training set data to produce a separate Gaussian definition of clusters for each of the plurality of active genotypes identified in (a).

In some implementations, adjusting the cluster positions of (d) includes updating the cluster positions using a Bayesian method. In some implementations, the updating includes: using the cluster positions identified by the first and second functions as prior, and obtaining posterior from the prior and the observed data of the training set. In some implementations, obtaining the posterior includes obtaining the posterior from the prior and a number, a central tendency, and variance of the observed data of the training set.

In some implementations, a method of genotyping a locus of a polyploid genome is provided. The method includes: receiving a first signal magnitude produced in a microarray by a first nucleotide type at the genomic locus, and receiving a second signal magnitude produced in a microarray by a second nucleotide type at the genomic locus, wherein the first and second signal magnitudes together identify a two-dimensional position for the locus genotype of the polyploid genome; comparing the two-dimensional position to a plurality of cluster positions in a cluster model for the genomic locus, wherein the cluster positions were produced by any methods as described above; and assigning a genotype to the genomic locus based on the distance between the locus genotype of the polyploid genome and the nearest cluster position in the cluster model.

In some implementations, the method further includes assigning a score to the assigned genotype. In some implementations, assigning the score includes calculating the score from an expression using (i) the distance between the locus genotype of the polyploid genome and the nearest cluster position in the cluster model, and (ii) a distance between the locus genotype of the polyploid genome and the second nearest cluster position in the cluster model. In some implementations, the method further includes exposing a sample of the polyploid locus to the microarray and measuring the first and second signal magnitudes. In some implementations, the microarray is a bead array.

Another aspect of the disclosure provides a method of producing a cluster model for genotyping polyploid organisms, the method including: fitting a plurality of parameters of a first function relating a first signal magnitude produced in a microarray by a first nucleotide type present in a first allele at a genomic locus of the polyploid organisms to a count of the first nucleotide type at the genomic locus; fitting a plurality of parameters of a second function relating a second signal magnitude produced in the microarray by a second nucleotide type present in a second allele at the genomic locus to a count of the second nucleotide type at the genomic locus; wherein fitting the plurality of parameters to the first and second functions is performed using a training set of the first and second signal magnitudes obtained by assaying the genomic locus for a plurality of organisms, and wherein the first and second functions together identify cluster positions for genotypes at the genomic locus; and adjusting the cluster positions identified by the first and second functions to more closely match observed data from the training set.

In some implementations, adjusting the cluster positions includes updating the cluster positions using a Bayesian method as described above.

Another aspect of the disclosure provides a method of producing a cluster model for genotyping polyploid organisms, the method including: identifying a plurality of active genotypes expected to be observed at a genomic locus of the polyploid organisms; fitting a plurality of parameters of a first function relating a first signal magnitude produced in a microarray by a first nucleotide type present in a first allele at the genomic locus to a count of the first nucleotide type at the genomic locus, wherein fitting the plurality of parameters of the first function assumes the identified plurality of active genotypes are observed in the polyploid genome; and fitting a plurality of parameters of a second function relating a second signal magnitude produced in the microarray by a second nucleotide type present in a second allele at the genomic locus to a count of the second nucleotide type at the genomic locus, wherein fitting the plurality of parameters of the second function assumes the identified plurality of active genotypes are observed in the polyploid genome; wherein fitting the plurality of parameters to the first and second functions is performed using a training set of the first and second signal magnitudes obtained by assaying the genomic locus for a plurality of organisms, an wherein the first and second functions together identify cluster positions for genotypes at the genomic locus.

In some implementations, identifying the plurality of active genotypes includes identifying fewer than all possible combinations of the first and second nucleotide types at the genomic locus. In some implementations, the polyploid genome is an allopolyploid genome. In some implementations, the polyploid genome is an allotetraploid genome and only three active genotypes are identified.

In some implementations, at least one of the first and second functions has the form:

$$\text{intensity}_a = x*(\text{counts}_{\text{allele } a})^y + z$$

wherein x, y, and z are adjustable parameters, $\text{intensity}_a$ is the first signal magnitude produced in the microarray, and $\text{counts}_{\text{allele } a}$ is the count of the first nucleotide type at the genomic locus. In some implementations, both the first and second function has the form above. In some implementations, at least one of the first and second functions is a non-linear function.

The disclosed embodiments also provide a computer program product including a non-transitory computer readable medium on which is provided program instructions for performing the recited operations and other computational operations described herein.

Some embodiments provide a system for genotyping polyploid SNPs (single nucleotide polymorphisms). The system includes a sequencer for receiving nucleic acids from the test sample providing nucleic acid sequence information from the sample, a processor; and one or more computer-readable storage media having stored thereon instructions for execution on the processor to evaluate copy number in the test sample using the method recited herein.

Another aspect of the disclosure provides systems for genotyping polyploid organisms. In some implementations, a system includes: a microarray configured to generate a first signal in response to contact with a first nucleotide type present in a first allele at a genomic locus of the polyploid organisms and generate a second signal in response to contact with a second nucleotide type present in a second allele at the genomic locus of the polyploid organisms; and one or more processors. The processors are configured to (i) receive data representing magnitudes of the first and second signals produced in a microarray in response to contact with the first and second nucleotide types at the genomic locus, wherein the first and second signal magnitudes together identify two-dimensional positions for the polyploid organisms; (ii) determine a plurality of cluster positions of a cluster model; (iii) compare the two-dimensional positions of the polyploid organisms to the plurality of cluster positions determined by the cluster model for the genomic locus; and (iv) assign genotypes to the polyploid organisms at the genomic locus based on the distance between the two-dimensional positions of the polyploid organisms and the nearest cluster position in the cluster model.

The plurality of cluster positions of the cluster model are obtained by: (a) identifying a plurality of active genotypes expected to be observed at the genomic locus in the polyploid organisms; (b) fitting a plurality of parameters of a first function relating the first signal magnitude to a count of the first nucleotide type at the genomic locus, wherein fitting the plurality of parameters of the first function assumes the identified plurality of active genotypes are observed in the polyploid organisms; (c) fitting a plurality of parameters of a second function relating the second signal magnitude to a count of the second nucleotide type at the genomic locus, wherein fitting the plurality of parameters of the second function assumes the identified plurality of active genotypes are observed in the polyploid organisms, wherein fitting the plurality of parameters to the first and second functions is performed using a training set of the first and second signal magnitudes obtained by assaying the genomic locus of a plurality of polyploid organisms, and wherein the first and second functions together identify cluster positions for genotypes at the genomic locus.

In some implementations, the cluster positions were produced by any of the methods described above.

In some implementations, the one or processors are further configured to assign a score to the assigned genotype. In some implementations, the one or processors are further configured to assign the score by calculating the score from an expression using (i) the distance between the locus genotype of the polyploid genome and the nearest cluster position in the cluster model, and (ii) a distance between the locus genotype of the polyploid genome and the second nearest cluster position in the cluster model. In some implementations, the microarray is a bead array.

In some implementations, the plurality of cluster positions of the cluster model are obtained by: (a) fitting a plurality of parameters of a first function relating the first signal magnitude to a count of the first nucleotide type at the genomic locus, (b) fitting a plurality of parameters of a second function relating the second signal magnitude to a count of the second nucleotide type at the genomic locus, wherein fitting the plurality of parameters to the first and second functions is performed using a training set of the first and second signal magnitudes obtained by assaying the genomic locus of a plurality of polyploid organisms, and wherein the first and second functions together identify cluster positions for genotypes at the genomic locus; and (c) adjusting the cluster positions identified by the first and second functions to more closely match observed data from the training set.

In some implementations, the plurality of cluster positions of the cluster model are obtained by: (a) identifying a plurality of active genotypes expected to be observed at the genomic locus in the polyploid organisms; (b) fitting a plurality of parameters of a first function relating the first signal magnitude to a count of the first nucleotide type at the genomic locus, wherein fitting the plurality of parameters of the first function assumes the identified plurality of active genotypes are observed in the polyploid organisms; and (c) fitting a plurality of parameters of a second function relating the second signal magnitude to a count of the second nucleotide type at the genomic locus, wherein fitting the plurality of parameters of the second function assumes the identified plurality of active genotypes are observed in the polyploid organisms, wherein fitting the plurality of parameters to the first and second functions is performed using a training set of the first and second signal magnitudes obtained by assaying the genomic locus of a plurality of polyploid organisms, and wherein the first and second functions together identify cluster positions for genotypes at the genomic locus.

Although the examples herein concern humans and the language is primarily directed to human concerns, the concepts described herein are applicable to genomes from any plant or animal. These and other objects and features of the present disclosure will become more fully apparent from the following description and appended claims, or may be learned by the practice of the disclosure as set forth hereinafter.

DETAILED DESCRIPTION

Definitions

Figure 1:
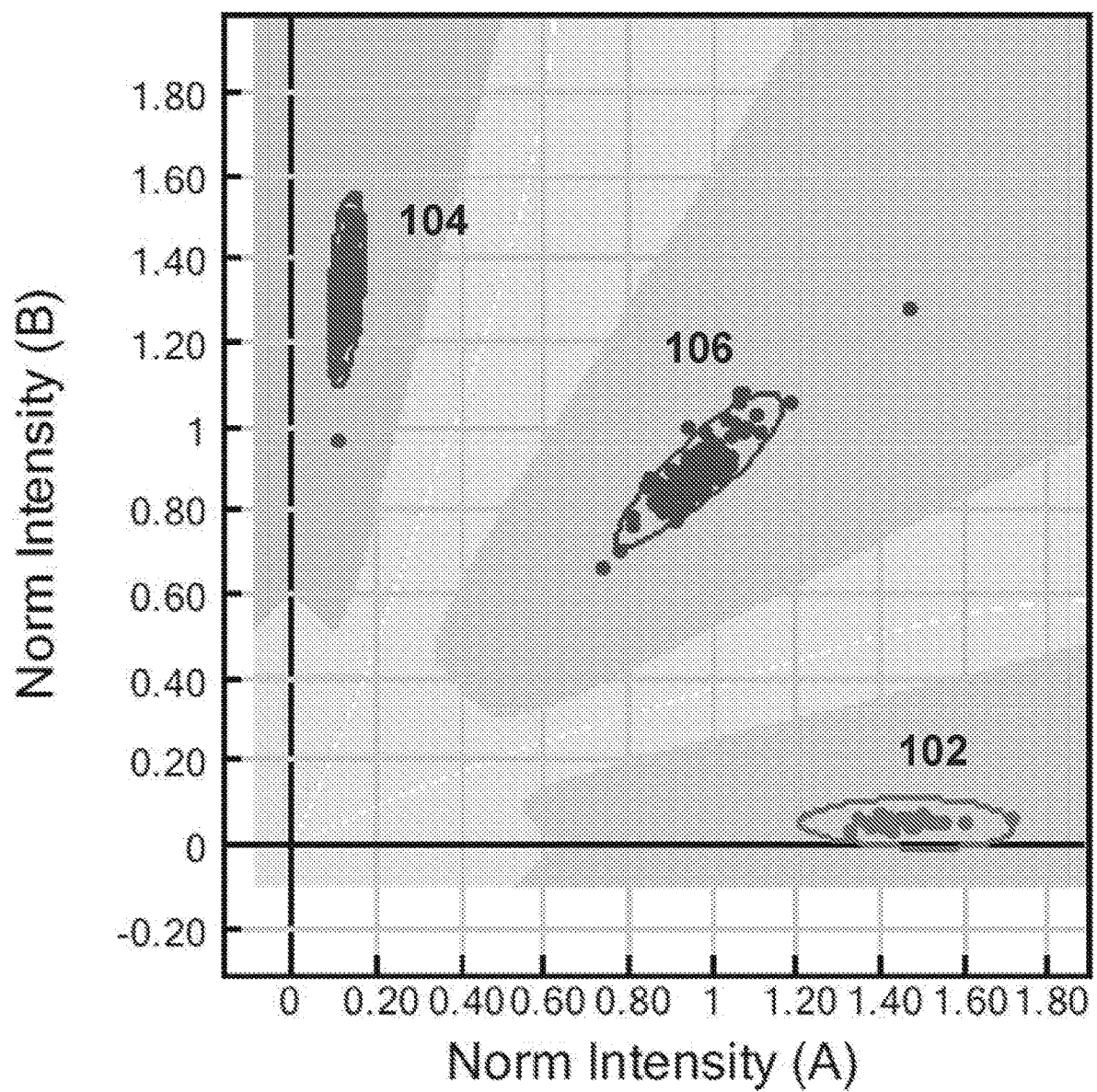
FIG. 1 shows clusters of example data from a two-channel microarray platform.

Unless otherwise indicated, the practice of the method and system disclosed herein involves conventional techniques and apparatus commonly used in molecular biology, microbiology, protein purification, protein engineering, protein and DNA sequencing, and recombinant DNA fields, which are within the skill of the art. Such techniques and apparatus are known to those of skill in the art and are described in numerous texts and reference works.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the Specification as a whole. It is to be understood that this disclosure is not limited to the particular methodology, protocols, and reagents described, as these may vary, depending upon the context they are used by those of skill in the art. As used herein, the singular terms "a," "an," and "the" include the plural reference unless the context clearly indicates otherwise.

Ploidy is a measure of the number of chromosomes in a cell or organism.

Haploid cells and organisms are those containing one set of chromosomes. The number of chromosomes in a haploid cell is known as the haploid number, often denoted as n.

Diploid cells and organisms are those containing two sets of chromosomes. The chromosome number of a diploid cell can be denoted as 2n. For instance, in humans, a diploid species, the haploid number n is 23, and the chromosome number 2n=46.

Polyploid cells and organisms (or polyploids) are those containing more than two sets of chromosomes. For instance, tetraploid cells and organisms have four sets of chromosomes, with 4n chromosomes.

Polyploidy involves a change in a complete set of chromosomes (above two sets). In comparison, an organism in which a single chromosome or chromosome segment is under- or over-represented is referred to as aneuploid. An organism in which a chromosome segment is under- or overrepresented is referred to as partially aneuploid. In other words, aneuploidy refers to a numerical change in part of the chromosome set, whereas polyploidy refers to a numerical change in the complete set of chromosomes.

Autopolyploids are polyploids with multiple chromosome sets derived from a single species. Autopolyploids can arise from spontaneous, naturally occurring genome duplications, such as in potatoes. Autopolyploidy can also form following fusion of unreduced gametes. One example of an autopolyploid is potato.

Allopolyploids are polyploids having chromosomes originated from different species. One example is durum wheat.

Because the multiple sets of chromosomes in autopolyploids originate from the same species, each set of the multiple sets can be combined with any other set of the multiple sets during meiosis. This is known as multi-valence. In comparison, because allopolyploid chromosomes originate from two different species, the chromosomes from the two different species often do not pair or recombine during meiosis. Only two chromosomes originate from the same species can pair and recombine during meiosis. This has implications for genotyping organisms.

Although in general autopolyploids tend to be multivalent and allopolyploids tend be bivalent, it has been shown that different degrees of valence exist for both autopolyploids and allopolyploids, resulting in different degrees of recombination and genotypes. The nature of the different genotypes may be accounted for using the methods and systems described herein to provide improved genotyping results.

The term "genotype" refers to the genetic makeup of a genome of a cell, an organism, or an individual, which may affect the specific characteristic or phenotype of the cell, organism, or individual.

The term "genotyping" refers to the determination of the genetic makeup of a cell or an organism. The term "SNP genotyping" refers to determining the alleles of one or more single nucleotide polymorphisms (SNPs) of a cell or an organism.

The term genotype typically implies a measurement of how an individual is different from others within a group of individuals of a species. When used in the context of a particular gene of interests, in polyploid individuals, genotype may refer to what combination of alleles the individual carries. When used in other broader contexts, such as genotyping for a phenotype or whole genome genotyping, a plurality of SNPs and genes are often involved.

In the context of genotyping, the phrase "allele count" is used herein to refer to the number of alleles per genomic locus (or simply "locus"). For instance, for a tetraploid individual at a bi-allelic location, there can be 0, 1, 2, 3, or 4 copies of allele A (e.g., having a nucleotide type), and corresponding 4, 3, 2, 1, or 0 copies of allele B. In other words, for polyploidy with X sets of chromosomes, there can be X+1 genotypes.

Related to the concept of allele count as mentioned above, the term genotype may be used to refer to the combination of alleles in a locus, a region, or a genome of an individual.

The term allele count in some context may refer to the number of DNA molecules having an allele in a processed sample. This quantity is proportional to the number of alleles per locus as described above, and also dependent on experimental conditions affecting the total number of molecules provided and measured in an experimental procedure.

The allele count for a SNP locus can refer to a normal number of copies of an allele at a genomic locus. In an example of a tetraploid, the allele count maybe 0, 1, 2, 3, or 4. In contrast, copy number of a copy number variation generally refers to an abnormal number of copies of a sequence. So in a tetraploid example as described above, an abnormal copy number may be more or less than four. The abnormal number of copies of sequence in a CNV situation may come from an additional number of a complete or partial chromosome. Moreover, the abnormal addition or subtraction of one or more copies of a sequence of interest in a CNV may occur as insertion or deletion of a sequence without affecting chromosome structure.

Zygosity is the degree of similarity of alleles for a locus of interest or a sequence of interest. Diploid organisms have the same loci on each of the two sets of homologous chromosomes, except that the sequences in these loci may differ between the two chromosomes in the matching pair. If both alleles of a diploid organism are the same, it is homozygous at that locus. If they are different, the organism is heterozygous at that locus. If one allele is missing, it is hemizygous. If both alleles are missing, it is nullizygous. Sometimes the term zygosity is also used to refer to the allele composition at a locus for a diploid organism. However, for polyploid organism, allele counts can provide more information about the genotype of an individual than zygosity can.

The term "parameter" herein refers to a numerical value that characterizes a property of a system such as a physical feature whose value or other characteristic has an impact on a relevant condition such as a sample. In some cases, the term parameter is used with reference to a variable that affects the output of a mathematical relation or model, which variable may be an independent variable (i.e., an input to the model) or an intermediate variable based on one or more independent variables. Depending on the scope of a model, an output of one model may become an input of another model, thereby becoming a parameter to the other model.

The terms "polynucleotide," "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The nucleotides include sequences of any form of nucleic acid, including, but not limited to RNA and DNA molecules such as cfDNA molecules. The term "polynucleotide" includes, without limitation, single- and double-stranded polynucleotide.

The term "test sample" herein refers to a sample, typically derived from a biological fluid, cell, tissue, organ, or organism, comprising a nucleic acid or a mixture of nucleic acids. Such samples include, but are not limited to sputum/oral fluid, amniotic fluid, blood, a blood fraction, or fine needle biopsy samples (e.g., surgical biopsy, fine needle biopsy, etc.), urine, peritoneal fluid, pleural fluid, and the like. Although the sample is often taken from a human subject (e.g., patient), the assays can be used to SNVs or CNVs in samples from any mammal, including, but not limited to dogs, cats, horses, goats, sheep, cattle, pigs, etc. The sample may be used directly as obtained from the biological source or following a pretreatment to modify the character of the sample. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc. If such methods of pretreatment are employed with respect to the sample, such pretreatment methods are typically such that the nucleic acid(s) of interest remain in the test sample, sometimes at a concentration proportional to that in an untreated test sample (e.g., namely, a sample that is not subjected to any such pretreatment method(s)). Such "treated" or "processed" samples are still considered to be biological "test" samples with respect to the methods described herein.

The term "training set" herein refers to a set of training samples that can comprise samples having various genotypes at one or more loci and are used to develop a model for analyzing test samples.

A training set may be a statistical sample in a population of interest. A statistical sample often comprises multiple individuals, data of which individuals are used to determine one or more quantitative values of interest generalizable to the population. The statistical sample is a subset of individuals in the population of interest. The individuals may be persons, animals, tissues, cells, other biological samples (i.e., a statistical sample may include multiple biological samples), and other individual entities providing data points (e.g., hybridization signal strength for one or more alleles) for statistical analysis.

A training set is often used in conjunction with a validation set. The term "validation set" is used to refer to a set of individuals in a statistical sample, data of which individuals are used to validate or evaluate the quantitative values of interest determined using a training set.

A microarray comprises a collection of spots immobilized on a surface of a substrate made of glass, plastic, or silicone, nylon, etc. The spots can be DNA, cDNA, or other oligonucleotides attached to, e.g., wells or beads in wells. Microarrays may be used to measure, e.g., the expression levels of a large numbers of genes, detect a large number of DNA sequences of interest, or to genotype multiple regions of a genome. Each spot contains a plurality of copies of a specific oligonucleotide sequence, known as probes (or reporters or oligos). Probes are used to hybridize with target nucleic acid sequences of interest in a sample. Probe-target hybridization is detected and quantified using fluorophore, chemiluminescence, silver, and other methods to determine relative abundance of nucleic acid sequences of interest in the sample. In some contexts, microarrays provide sequences of a portions of sequences of nucleic acid samples and therefore may be considered sequencers.

The term "based on" when used in the context of obtaining a specific quantitative value, herein refers to using another quantity as input to calculate the specific quantitative value as an output.

As used herein the term "chromosome" refers to the heredity-bearing gene carrier of a living cell, which is derived from chromatin strands comprising DNA and protein components (especially histones). The conventional internationally recognized individual human genome chromosome numbering system is employed herein.

The term "subject" herein refers to a human subject as well as a non-human subject such as a mammal, an invertebrate, a vertebrate, a plant, a fungus, a yeast, a bacterium, and a virus. Although the examples herein concern humans and the language is primarily directed to human concerns, the concepts disclosed herein are applicable to genomes from any plant or animal, and are useful in the fields of crop agriculture, veterinary medicine, animal sciences, research laboratories and such.

The term "sensitivity" as used herein refers to the probability that a test result will be positive when the condition of interest is present. It may be calculated as the number of true positives divided by the sum of true positives and false negatives.

The term "specificity" as used herein refers to the probability that a test result will be negative when the condition of interest is absent. It may be calculated as the number of true negatives divided by the sum of true negatives and false positives.

Genotyping Technology

This disclosure provides improved methods, systems, and computer products for genotyping polyploid organisms, as well as diploid organisms. In various implementations, an allele-intensity model is used to generate the cluster definitions. The allele-intensity model relates the allele counts of different genotypes to signal intensities generated by the genotyping platform. In some implementations, the model also includes the capability to update cluster positions obtained from a maximum likelihood model using a Bayesian method.

The methods and systems disclosed herein are suitable for various genotyping applications. In some implementations, the methods are suitable for whole-genome SNPs genotyping. Various technology platforms can be used to implement the disclosure. For instance, microarrays may be used to provide data for genotyping sequence of interest. On these and other platforms two or more channels of data are provided to measure the quantity and indicate the identity of different nucleotides associated with SNPs of interest. Because different organisms have different inheritance and genotype characteristics, they provide different clusters of microarray data.

For instance, on the Illumina Infinium™ platform, different nucleotides are indicated by red and green light detected by the imaging system, where the red light intensity measures the number of molecules for one nucleotide of a SNP, and the green light intensity measures the number of molecules for another nucleotide of the same SNP. When data of the red and green light channels are plotted on a two-dimensional plot, data points for samples form clusters for different genotypes. For instance, for a biallelic SNP, three clusters are formed for AA, AB, and BB genotypes.

Conventional clustering methods can define clusters for a biallelic SNPs in diploid organisms. However the genotypes and corresponding clusters of micro-array data for polyploid samples are different from diploid samples, and conventional methods need improvements for defining the clusters corresponding to different genotypes of the polyploid samples. The typical solution to this problem would be k-means clustering or another approach related to mixture modeling of distributions. However, these traditional cluster model generation approaches per se typically do not use genotype information to predict and/or use the locations of clusters.

The disclosed methods and systems allow identification and definition of clusters that are suitable for different polyploid genotypes. In some implementations, the methods provided herein allow for customization of ploidy number as well as the nature of polyploidy. In some implementations the method includes the ability to customize the genotypes used in the model that is built to fit the training data. The customization of the genotypes can be based on the characteristics of the genome that are known. In some implementations the method includes the capability to learn to discriminate cluster positions in two dimensions such as in allele signal strength and type. In one example, sequence data is provide in polar coordinates, with R (radius) representing signal strength or intensity and angle (theta) representing allele type (e.g., A or B, or T or C). In some implementations the method includes the ability to update cluster positions from maximum likelihood estimates using a Bayesian approach. In some implementations, the disclosure provides improved sensitivity and/or specificity to genotyping results, due to at least in part on the clustering definitions that better capture data variance within or across genotypes compared to conventional clustering methods. The features and advantages of the implementations are further described hereinafter.

Genotyping Polyploid Organisms

Genotyping polyploidy species has been a challenge for sequencing technologies such as micro-array data analysis, especially in the absence of a large amount of training data. The disclosed methods in some implementations provide an approach that works both on a limited amount of data and can improve as more data are included to train and improved the model used to generate the clusters for different possible genotypes.

As mentioned above, in some implementations microarray platforms provide data for genotyping various organisms with different genotypes. In general, these platforms provide two or more channels of data representing the identities and relative quantities (e.g., counts) of nucleotides that are measured.

In some implementations, nucleotides are labeled with color dyes such as fluorescent dyes. For instance two different colors may be used to label two different nucleotides of a specific SNP of interest. When the nucleotides corresponding to a specific SNP are measured by an imaging device, the intensity and the colors will indicate the quantity and identity of the two nucleotides corresponding to two alleles. When the data of different genotypes are shown in a two-color space, they form distinguishable clusters. In some implementations, depending on the sequencing technology, instead of colors or electromagnetic wavelengths, different ion concentrations may be used to indicate the identities and quantities of the different nucleotides associated with the different alleles. In another implementation, instead of using two colors to label two different nucleotides of two alleles, four different colors may be used to label four different nucleotides, generating four channels of data to discriminate among all four different nucleotides. In another implementation, the two channels of data can be implemented as two physical probes (e.g., two bead types) targeting the same SNP locus but different alleles, therefore the relative intensity of the two different probes indicates the allele frequency and genotype of the SNP.

In some implementations micro array technology is used to provide sequence/allele signal. For example, bead array technology may be used to provide SNP genotyping, over the whole genome or a portion thereof. In some implementations the Illumina Infinium™ platform is used, which includes hundreds of thousands to millions of micro-wells on a beadchip, and microbeads are distributed in the microwells. The microbeads have diameters of roughly 3 µm. DNA samples are processed, amplified, and provided to the beadchip. Each bead is covered with hundreds of thousands of copies of a specific oligonucleotide that acts as capture sequences targeting different SNPs. The captured DNA fragments are used as the template to grow the oligonucleotides on the bead. The nucleotide added to the oligonucleotide is complementary to the captured DNA fragment and indicates the identity of the nucleotide of the specific allele on the captured nucleic acid fragment. The nucleotide corresponding to the allele is measured by an imaging device such as the Illumina iScan™ system. The image data having red and green signals of different intensities can then be plotted to form clusters in the data space or compared to clusters to determine genotypes.

In some implementations the Illumina Infinium™ or Golden Gate™ microarrays may be used to provide the genotyping data. These and other platforms produce two-colored readouts (one color for each allele) for each single nucleotide polymorphism in the genotyping study. Intensity values for each of the two color channels, A and B, convey information about the allele ratio at a locus. FIG. 1 shows clusters of example data from a two-channel microarray platform. Shown in FIG. 1 on the horizontal axis is the normalized intensity of data corresponding to the first allele A. Shown on the vertical axis is the normalized intensity for channel B corresponding to allele B. The cluster 102 near the horizontal axis includes samples having only allele A, and therefore having the genotype of AA at the specific locus. The cluster 104 near the vertical axis of data includes samples having only allele B, and therefore having the genotype BB. The cluster 106 includes data points for samples that have both allele A and allele B, corresponding to genotype AB at the locus.

Many applications incorporate values for a large number of samples (hundreds to tens of thousands) to ensure significant statistical representation. When these values are appropriately normalized and plotted, distinct patterns or clusters emerge, in which samples that have identical genotypes at an allele locus exhibit similar signal profiles (A and B values). In contrast, samples with differing genotypes will appear in separate distinct clusters. For diploid organisms, biallelic loci are expected to exhibit the three clusters: AA, AB, and BB.

Figure 2:
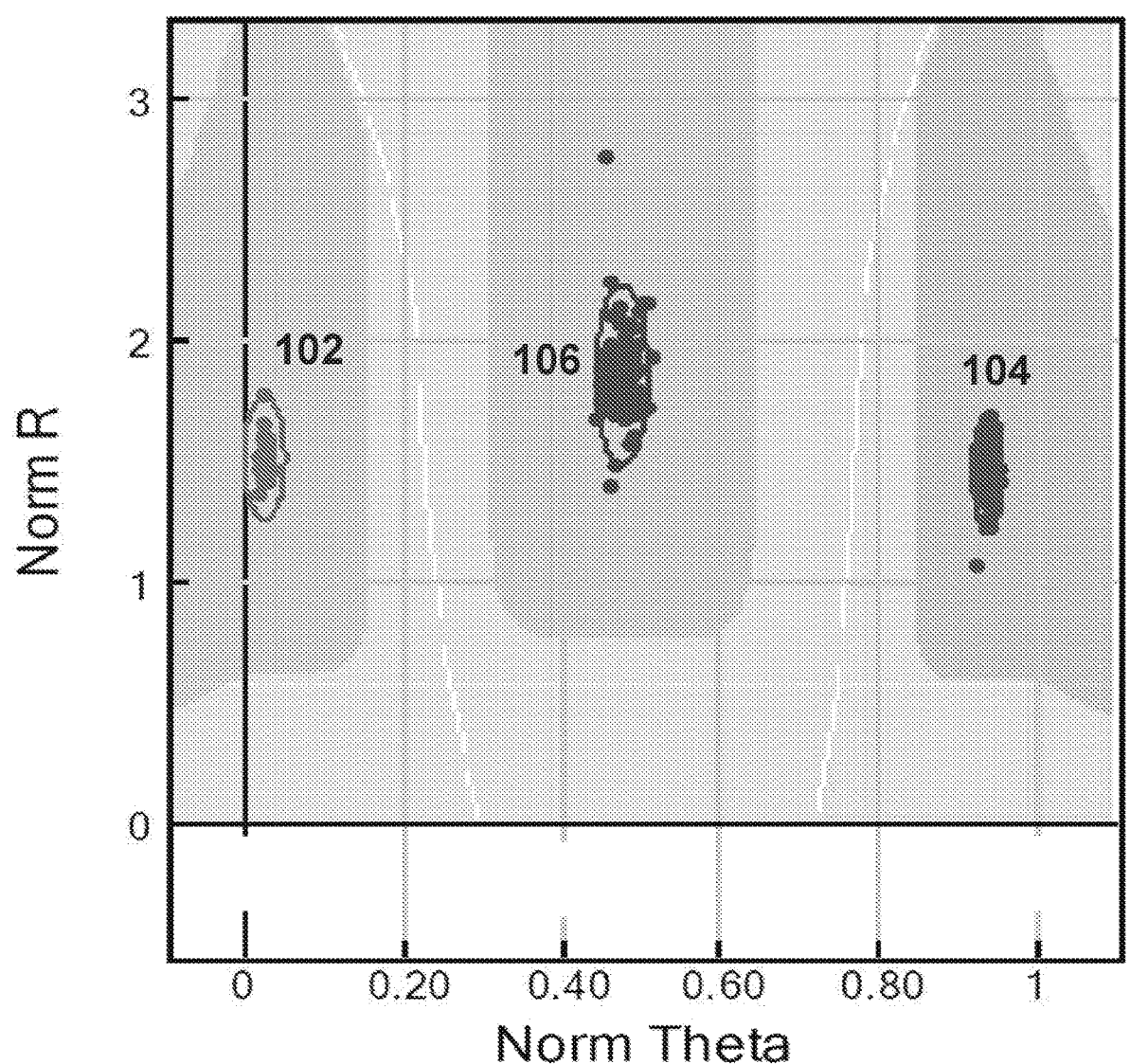
FIG. 2 shows clusters of data based on the same data from the two-channel microarray platform as in FIG. 1 but transformed to polar coordinates.

Various methods identify these clusters and use the cluster definitions for downstream genotype calling. The signals of A and B channels obtained from a collection of DNA samples serve as input values for developing clusters. Clusters corresponding to these signals can be characterized by five parameters: mean of A intensities, mean of B intensities, standard deviation of the A intensities, standard deviation of B intensities, and covariance of A and B intensities. In many samples, the covariance parameter is only significant for the AB cluster, because the AA and BB clusters mostly lie along their respective axis. In certain embodiments, to simplify the clustering process or the visualization thereof, the analysis transforms A and B intensities into two new values, labeled θ and R. FIG. 2 shows clusters of data based on the same data from the two-channel microarray platform as in FIG. 1 but transformed to polar coordinates. The data shown in FIG. 1 are transformed and plotted in FIG. 2. θ quantifies the relative amount of signal measured by the A and B intensities, defined by the equation:

$$\theta = 2\pi^{-1} \arctan(AB^{-1})$$

R is the measurement of the total intensity observed for from the A and B signals, defined as:

$$R = A + B$$

As seen in FIG. 2, the three clusters shown in polar coordinate corresponding to the same data in clusters in FIG. 1. Here cluster 102 corresponds to genotype AA, with cluster 104 corresponding to genotype BB, and cluster 106 corresponding to genotype AB. The θ values for the three clusters are about 0, 0.5, and 1.

Upon transformation of A and B values to the polar coordinates, θ and R, fewer parameters are needed to characterize a cluster. Since little correlation exists between θ and R, the cluster can be parameterized with just the mean and standard deviation for each of these two variables. These parameters for each cluster can be identified using various clustering techniques.

Conventional methods for clustering have limitations especially for polyploid samples. Polyploidy can arise through different mechanisms, e.g. by chromosome duplication in somatic cells or by meiosis of unreduced gametes. The origin of polyploidy has implications for genotyping. Autopolyploidy arises through duplication of a single genome of a single species. Allopolyploidy arises from the fusion of two different genomes of two species. For example potato is an auto tetraploid, while durum wheat is an allotetraploid arising from the hybridization of *T. urartu* and *A. speltoides*.

The origin of the duplicated chromosomes affects how traits are inherited and therefore on genotype of the organism. Specifically, allopolyploid genome exhibits a bivalent pairing of chromosomes, in which only the chromosome pair having the same origin would pair during meiosis. Conversely, an autopolyploid genome would exhibit multi-valent pairing of chromosomes, in which all duplicated chromosomes can jointly pair during meiosis. In the allopolyploidy case, one would not expect recombination across the chromosomes of different original species. Therefore, the inheritance pattern of an allopolyploid locus for an organism originating from a first species having a heterozygous SNP at the locus and a second species having a homozygous SNP will display an inheritance pattern similar to that of a diploid organism as further explained below.

Figure 3:
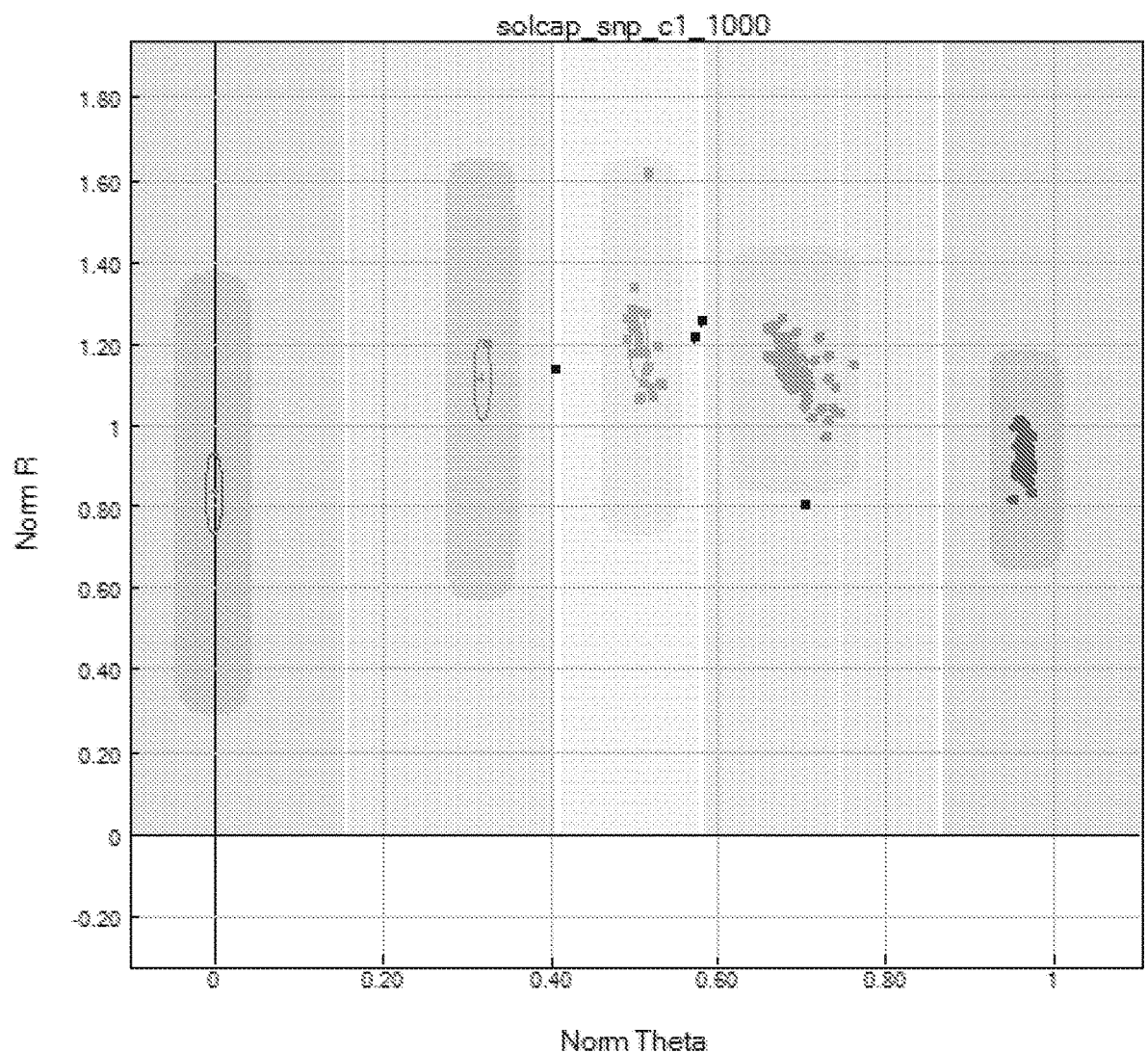
FIG. 3 shows clusters of data in the polar coordinate for a sample of autopolyploidy organisms.
Figure 4:
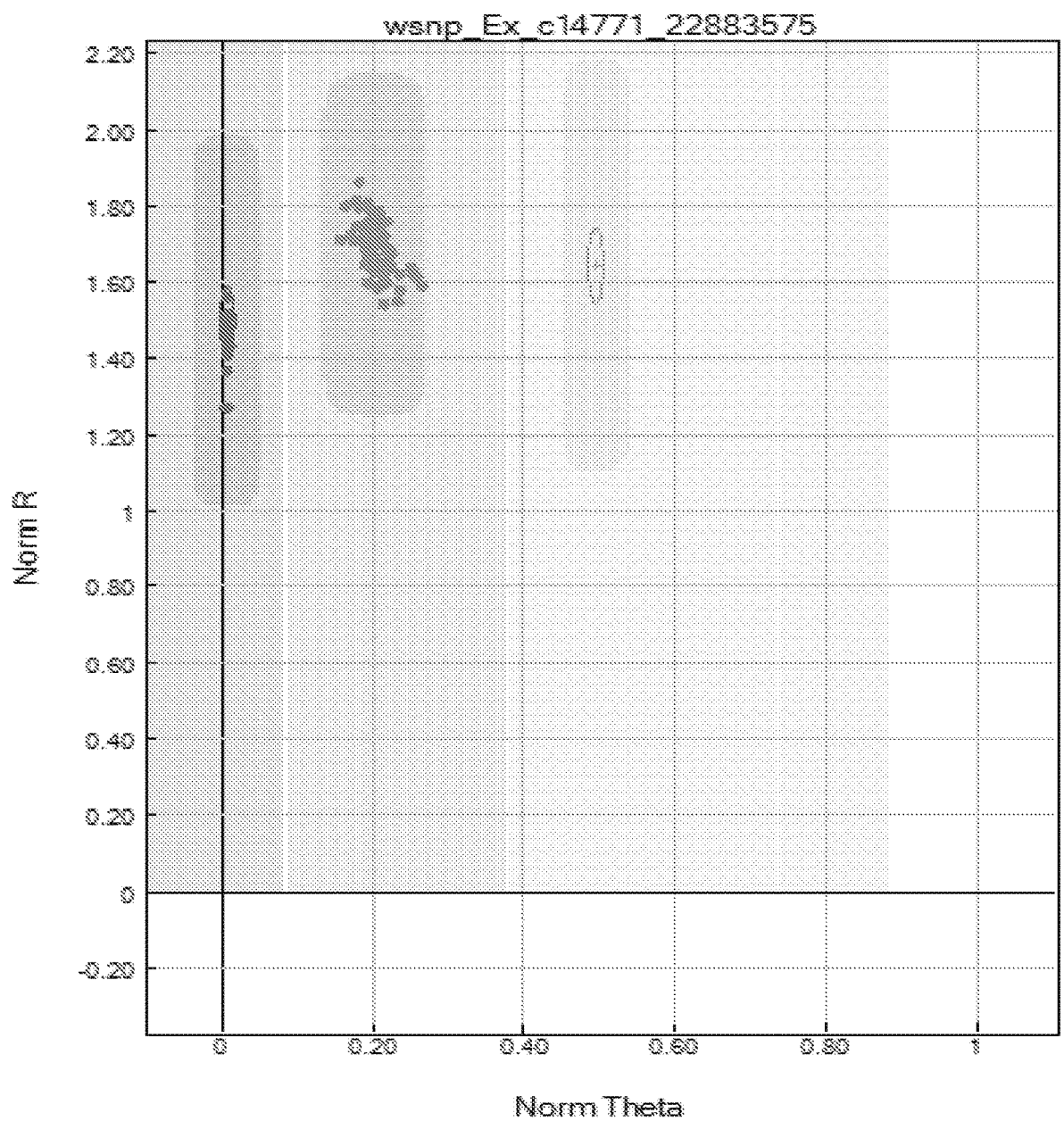
FIG. 4 shows clusters of data in the polar coordinate for a sample of allopolyploid organisms.

For an autopolyploid species, recombination across all duplicated chromosomes will lead to X+1 expected genotype clusters, where X is the ploidy number. See FIG. 3. FIG. 3 shows clusters of data in the polar coordinate for a sample of autopolyploidy organisms. For an allopolyploidy species, recombination across a single chromosome pair will lead to three expected genotype clusters, similar to a diploid locus, see FIG. 4. FIG. 4 shows clusters of data in the polar coordinate for a sample of allopolyploid organisms. The example shows clustering pattern of an organism that shows individuals of a species that originate from two species, with one of the original species having a homozygous SNP and other species having a heterozygous SNP.

Figure 5:
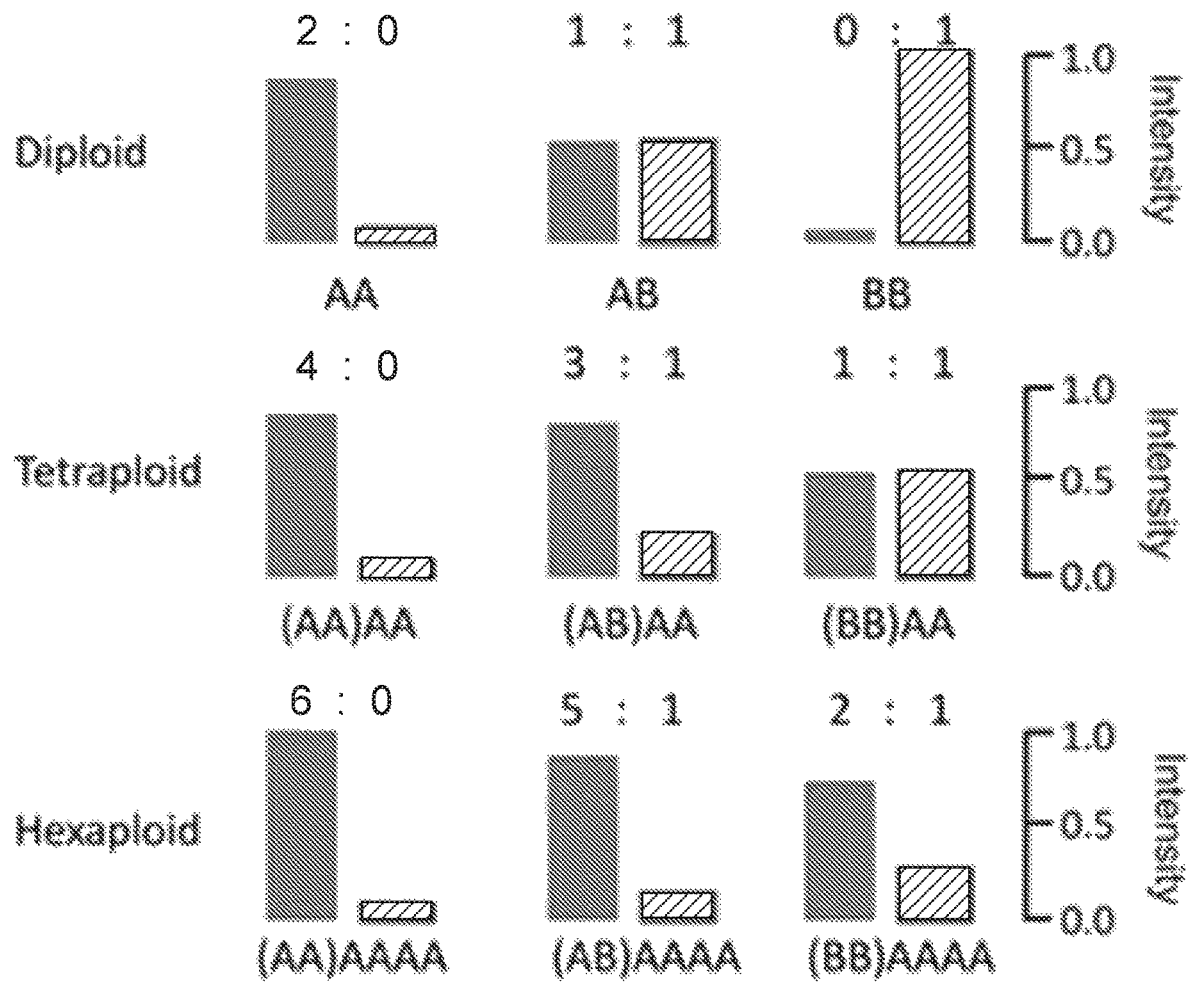
FIG. 5 schematically illustrates the allele ratios of a diploid species in the top row, the allele ratios of an allotetraploid species in the middle row, and those of a hexaploid species in the bottom row.

In the example given above, although the inheritance pattern of the allopolyploidy species is similar to that of a diploid species, the clusters in the allopolyploidy species is shifted relative to that of the diploid species. The θ values for the three clusters are about 0, 0.2, and 5 for the allotetraploids in FIG. 4. The θ values for the three clusters in FIG. 2 for a diploid sample are 0, 0.5, and 1. The underlying mechanism causing the shift can be illustrated by FIG. 5, which is based on FIG. 1(b) of Akhunov, Nicolet, and Dvorak (2009), Single nucleotide polymorphism genotyping in polyploid wheat with the Illumina GoldenGate assay, Theor Appl Genet., 119(3):507-17. The solid bars indicate the copy numbers or dosages of the A allele, and the hatched bars indicate the copy numbers or dosages of the B allele. Shown at the top row of FIG. 5 is a diploid organism. On the left of the top row is shown the AA genotype, having a 2 to 0 ratio of the A and B alleles. In the middle is shown the AB genome type, with the A and B alleles having a 1 to 1 ratio. On the right is shown the BB genotype, with the A and B alleles having a 0 to 2 ratio.

The middle row of FIG. 5 shows an allotetraploid example species mentioned above, originating from hybridization of a first species of AB genotype and a second species of AA genotype. Shown on the left is a sample having a (AA)AA genotype. The alleles shown in parenthesis originated from the heterozygous original species. The alleles AA originates from the homozygous original species. The two AA alleles from this homozygous original species are also referred to as the background allele or alleles of a background genome. For the (AA)AA phenotype shown on the left, allotetraploid individuals have a 4 to 0 ratio of the A and B alleles. For the genotype (AB)AA shown in the middle, the allele ratio is 3 to 1. For the (BB)AA genotype, the allele ratio is 1 to 1. Therefore, although the diploid species in the top row and the allotetraploid species in the middle row both have three genotypes, the allele ratios are different. Shown in the bottom row of FIG. 5 is a hexaploid species having a similar inheritance pattern for that of the diploid species in the top row and the tetraploid species in the middle row. This allohexaploid species originates from a heterozygous diploid original species and a homozygous tetraploid original species. The inheritance pattern of the allohexaploid species again is similar to that of the diploid. However, the A to B allele ratio in a sample of the genotype on the left is 6 to 0, the genotype in the middle has an A to B allele ratio of 5 to 1, and the genotype the right has an AB allele ratio of 2 to 1.

Although the inheritance pattern of the allotetraploid or hexaploid species are similar to those of the diploid species, hybridization of the assay probes to the background genome (e.g., AA from the homozygous original species in the example shown in FIG. 5) may impact the expected intensity of the three clusters of the three genotypes. In the example in FIG. 4, the BB cluster is located at a value of 0.5, due to the constant A allele signal from the chromosome pair of the homozygous original species AA as shown in the middle row of FIG. 5.

Figure 6:
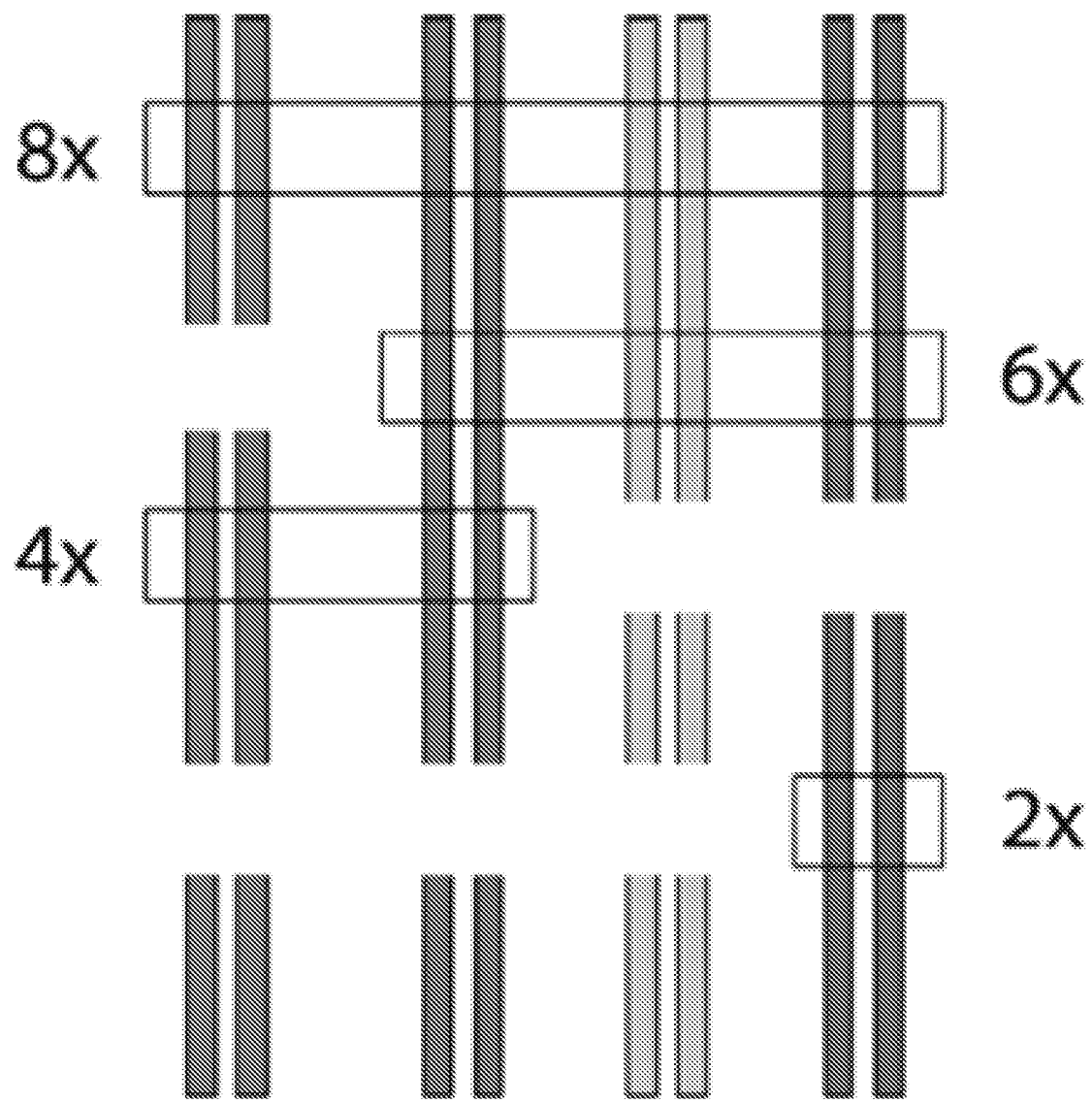
FIG. 6 illustrates how different loci in an octaploid sample have contributions from only a subset of all four chromosome pairs.

Despite this effect, it is not the case that every locus in the polyploid species would display this shifted data pattern. Some loci will behave more like a true diploid locus. This will occur when the allele has no activity on the other chromosome pairs, as would occur if the region including the SNP is deleted on the other chromosome pairs. See FIG. 6, which illustrates how different loci in an octaploid sample have contributions from only a subset of all four chromosome pairs. FIG. 6 is based on FIG. 15(a) of Bassil, et al. (2015) Development and preliminary evaluation of a 90 K Axiom® SNP array for the allo-octoploid cultivated strawberry Fragaria×ananassa. BMC Genomics 16:155.

With this knowledge, one can frame the genotyping algorithm to account for only those genotypes that are possible at given loci.

Despite the similarities to diploid genotyping, the shifted cluster positions of the polyploid species will cause genotyping errors if the data is processed with the diploid genotyping module. The methods and systems provided herein employ an allele-intensity model optimized for maximum likelihood, which is further described below. The model allows defining active clusters based on the active clusters for genotypes that are expected to be observed for a particular species (e.g., an allotetraploid). The expected genotype information may come from, e.g., prior knowledge about the species or organisms, or prior data obtained from the species or organisms.

As further described hereinafter, in some implementations, the model allows for customization of the number of alleles of different genotypes. In some implementations, the nature of the genotypes can be used to form the allele-intensity model. In some implementations, the allele-intensity model may be improved by accounting for both the distributions of the clusters and the amount of information available using a Bayesian method.

Preparing Models for Genotyping Organisms

Figure 7:
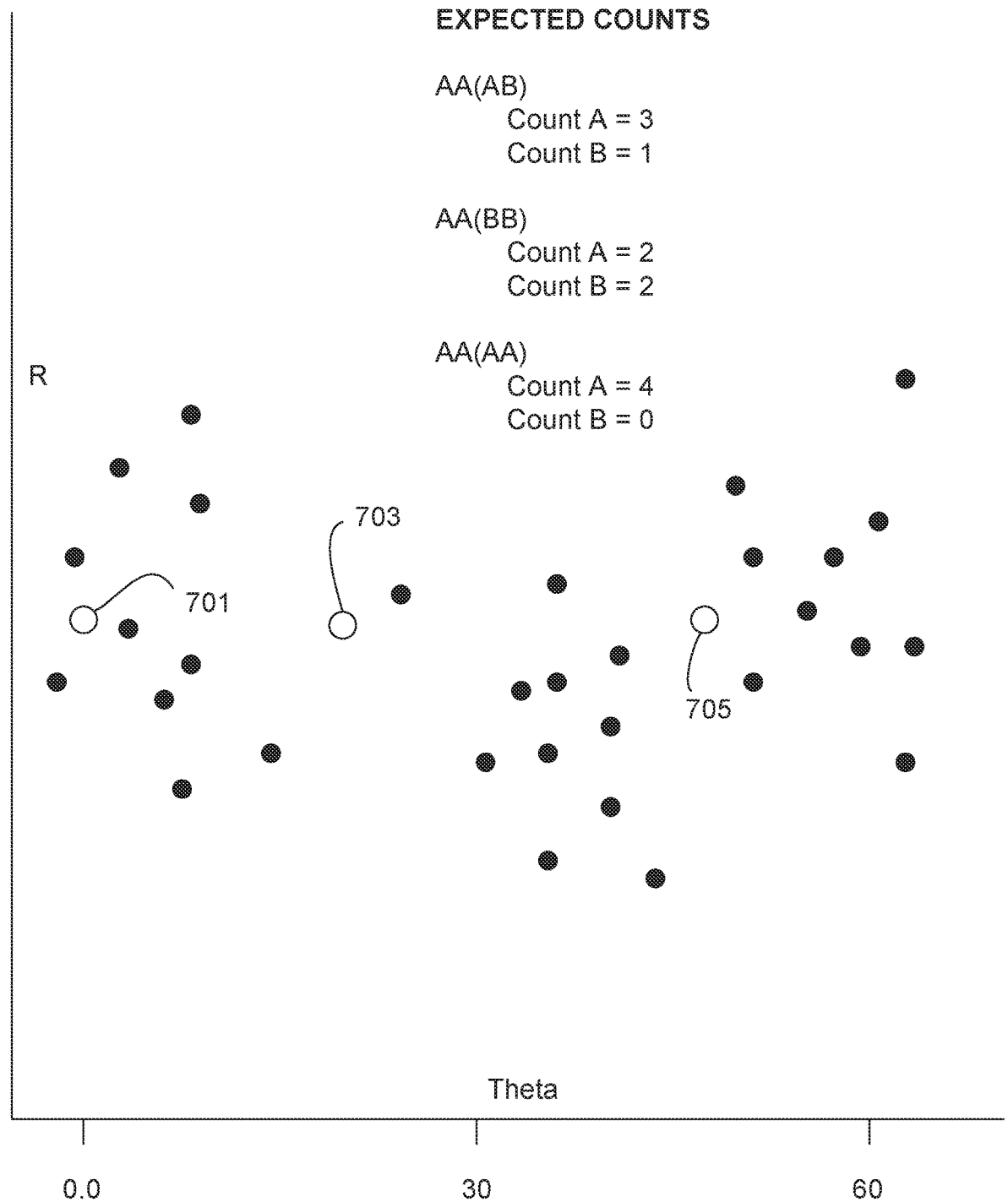
FIG. 7 depict a first stage of an example process for generating a clustering model for genotyping polyploid loci.
Figure 8:
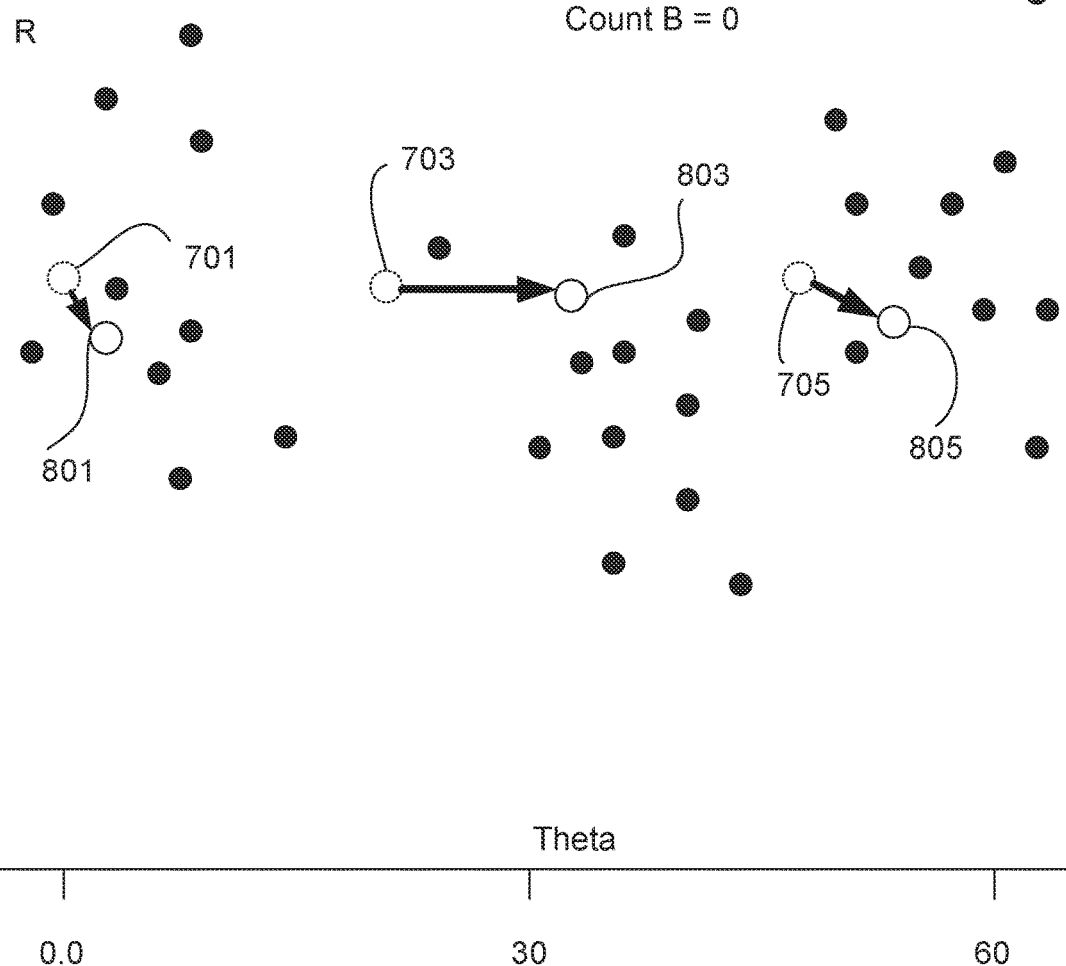
FIG. 8 depict a second stage of an example process for generating a clustering model for genotyping polyploid loci.
Figure 9:
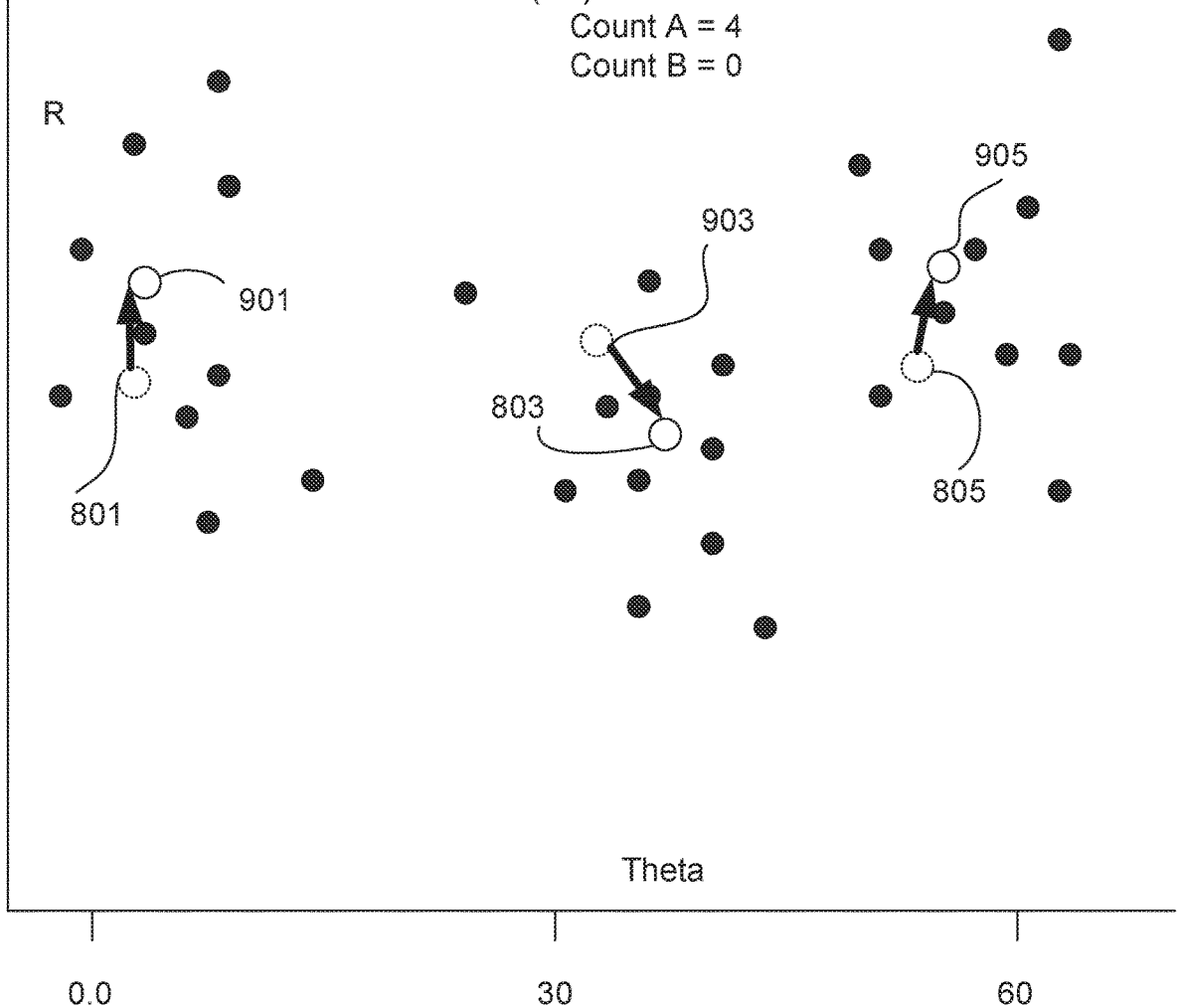
FIG. 9 depict a third stage of an example process for generating a clustering model for genotyping polyploid loci.
Figure 10:
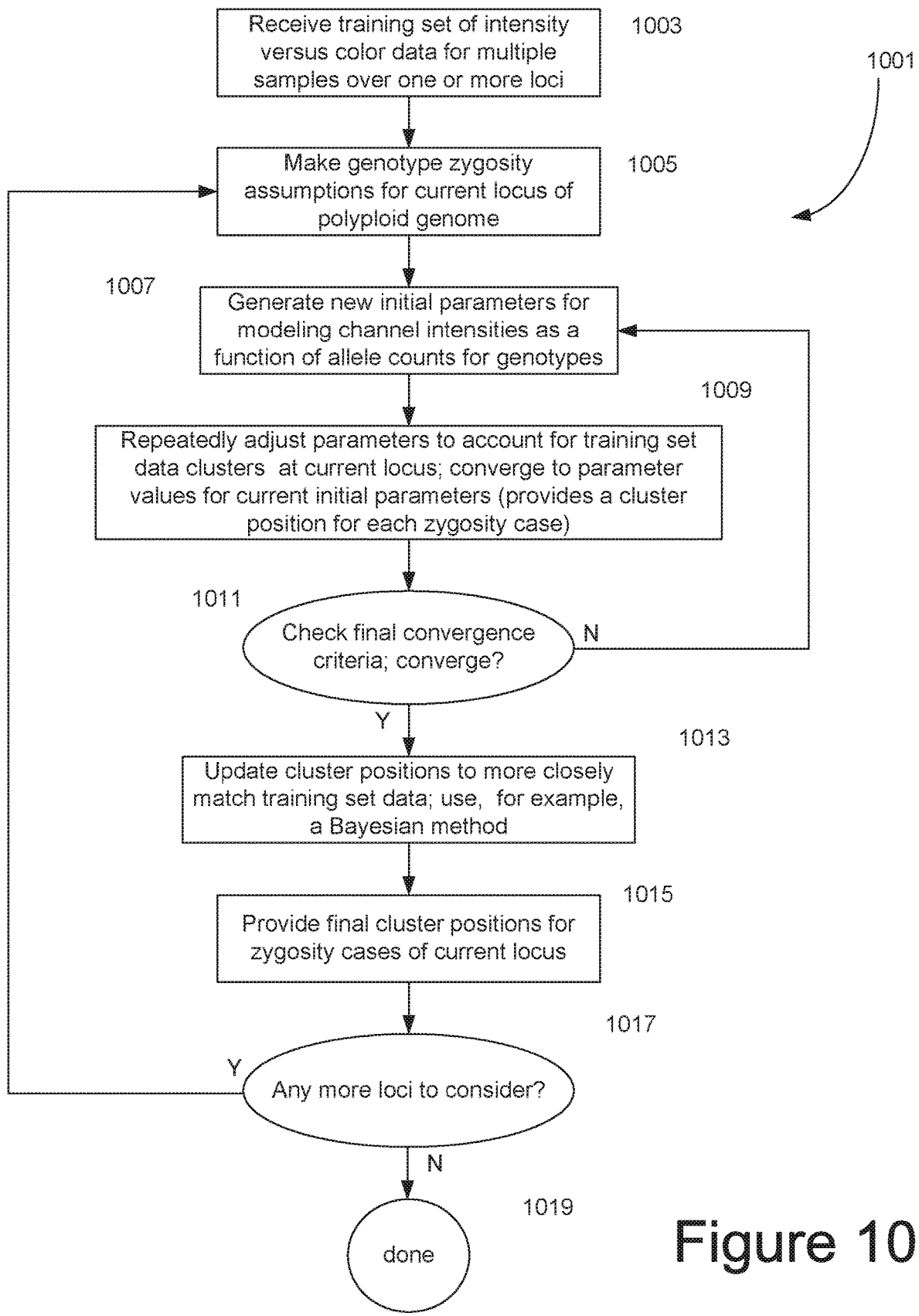
FIG. 10 presents a flowchart of operations that may be employed to generate a clustering model.

FIGS. 7, 8, 9, and 10 depict an example of a process for generating a clustering model for genotyping polyploid loci. FIG. 10 presents a flowchart of operations that may be employed to generate such a model. FIGS. 7, 8, and 9 present a hypothetical example illustrating how the choice of cluster positions for a model evolves or is optimized over the course of the model generation process. These figures show hypothetical training set data, depicted as black-filled dots, along with corresponding cluster locations, depicted as hollow circles, for the clustering model.

As shown in FIG. 10, a model generation process 1001 begins with an operation 1003 where the system that produces the model receives a training set of intensity versus color data for multiple samples used to train the model. The training set data may be provided over one or more loci of the polyploid organisms used to produce the training set. In certain embodiments, the organisms' actual genotypes at the one or more loci are unknown. In such cases, model generation is an unsupervised machine learning process. In other cases, the genotypes of the one or more loci are known, in which case model generation is a supervised machine learning process. While both options are possible, aspects of this disclosure will describe the process in terms of an unsupervised process.

While the examples presented herein refer to color versus intensity data for genotyping, the disclosed embodiments extend to other types of data that may be collected by sequencers or other types of genotyping apparatus. For example, wavelengths outside of the visible spectrum may be used for characterizing sequence data. For example, ultraviolet radiation in two different regions of the ultraviolet spectrum may be used for two channels representing different alleles (nucleotide types). Other embodiments employ non-radiation based signals such as ion concentrations measured in separate channels (each associated with one or two nucleotide species) or electrical current changes associated with distinct nucleotide species. In all cases, the signal can be viewed as providing a signal magnitude dimension (e.g., ion concentration, molecule count (e.g., hybridized molecules or sequenced molecules), or radiation intensity) and a nucleotides species dimension (e.g., color or time during exposure to a particular nucleotide species).

As shown in FIGS. 7, 8, and 9, the training set data is represented as black dots on a plot of R (radius) versus theta (angle of the data position between two orthogonal axes). The angular separation among theta values correspond to different zygosities or relative allele counts, which represent the proportions of each of two nucleotide types (A, T, C, G). As described above, in certain implementations, it is convenient to depict two channel data of varying magnitudes in polar coordinates using R and theta to represent clusters of the data. Other representations may be used such as Cartesian coordinates. In some embodiments, additional channels are employed, such as in a four channel genotyping apparatus that employs a separate channel for each of the four nucleotides.

As can be seen in FIGS. 7 through 9, the hypothetical training set data very coarsely distributes into three clusters of varying values of theta, centered around approximately 5°, 35°, and 50° (or in radians 0.09, 0.61, and 0.87)

The model generation process may employ certain genotype zygosity assumptions for any one or more of the loci used to genotype the polyploid genome of a species under consideration. See process operation 1005 of FIG. 10. For example, an allotetraploid genome locus may have three potential genotypes such as those shown in the upper portions of FIGS. 7, 8, and 9. As shown, the active genotype combinations include AA(AB), AA(BB), and AA(AA), where A and B are nucleotide types (A, T, C, G). At a locus having such active genotypes (zygosities), two of the four tetraploid chromosomes always have allele value A, while the other two chromosomes have diploid like zygosity options: homozygous A or B and heterozygous AB. Genotypes BB(AB) and BB(BB) are assumed not to occur. As explained above, standard diploid-centric genotyping methods are generally unsuitable for genotyping such loci in tetraploid organisms. As illustrated in FIGS. 7 through 9, the allele counts for such locus are 4:0, 3:1, and 2:2. As an initial approximation, these allele counts suggest that the ratios of intensity values from two channels of a two-channel genotyping apparatus are 4:0, 3:1, and 1:1. Using this assumption, the model generation process may initialize cluster locations for each of the active genotype possibilities as depicted in FIG. 7. In such cases, one might reasonably expect that the data clusters would center at theta values of approximately 0°, 18.4°, and 45° (in radians, 0, 0.32, and 0.79). This is depicted by cluster centers 701, 703, and 705 shown in FIG. 7.

As explained elsewhere, the cluster model may employ expressions for calculating expected signal intensity for each of two (or more) channels as a function of allele count. Such expressions may employ one, two, three, or more fittable parameters, which are adjusted during the model generation process to better match the cluster locations with the training set data. With this in mind, the model generation system generates initial parameters for modeling the channel intensities as a function of allele counts for the various genotype zygosities at a particular locus. See process block 1007 of FIG. 10. Effectively, the model generation process used to adjust or fit these parameters moves the cluster locations such as cluster locations 701, 703, and 705 to new positions that better agree with the relative positions of the training set data. In certain embodiments, model parameters are adjusted to maximize the fit (e.g., likelihood) or minimize the error (e.g., aggregate distance) between the modeled cluster positions and the training set points. To this end, the model generation process and system repeatedly adjust the parameters by performing, for example, a gradient method such as maximum likelihood estimation to account for the training set data clusters at the current locus. Suitable examples of such process are described below. The process continues until convergence of the parameter values for the current set of initial conditions (i.e., initial values of the parameters that are used to relate allele count to channel intensity). See process block 1009. Also see FIG. 8 in which the cluster positions 701, 703, and 705 move to improved positions 801, 803, and 805, respectively.

The techniques employed to adjust the parameters relating allele count to channel intensity may be susceptible to converging in local maxima or minima, depending on the optimization technique. To this end, the process may employ multiple different initial parameter values during the process of adjusting the parameters to find an optimal fit based upon the underlying biology/genetics and the training set data. This approach is represented in FIG. 10 where a decision operation 1011 determines whether enough initial parameter value sets (or iterations) have been considered to give confidence that one of them produces final parameter values that are at or near a global maximum or minimum. In certain embodiments, at least about five iterations are conducted. In certain embodiments, at least about ten iterations are conducted. If not, process control is directed back to process operation 1007 where the model generation system provides a new set of initial parameter values for the relationship between allele count and channel intensity. With these new initial parameter values, the system again repeatedly adjusts the parameter values to account for training set data clusters as described earlier and reflected in process operation 1009. When the current iteration of parameter value optimization converges locally, the system again checks at decision operation 1011 to determine whether a sufficient number of different initial parameter values have been considered. In some embodiments, rather than running a set number of iterations, each with different initial parameter values, the method may check the fit parameter values for one or more convergence criteria, which are designed to identify global maxima or minima.

Ultimately, the final convergence criteria are met and decision operation 1011 is answered in the affirmative. At this point, the parameter values for the relationships between channel intensity (or other signal magnitude measurement) and allele count are fixed. From here, a separate phase of the cluster position optimization may be performed. As an example, this additional phase updates the cluster positions provided by the parameter fit operations reflected in operations 1007, 1009, and 1011 to more closely relate those positions to the training set data. This second phase of the cluster positioning procedure may employ, for example, a Bayesian method. See operation 1013. Embodiments of this operation will be described in further detail below.

After the second phase of the cluster location process is complete, the model generation system defines the model for the current locus by the final cluster positions output from operation 1013. See process operation 1015. Operations 1013 and 1015 are exemplified in FIG. 9, where initially optimized cluster positions 801, 803, and 805 are further optimized to cluster positions 901, 903, and 905, respectively.

In certain embodiments, the model generation process is repeated for multiple loci of an organism. In such cases, training set data is provided for each locus and a separate model, with separate parameters (for channel signal magnitude versus allele count) and separate cluster positions, is provided for each locus. Depending on the polyploid organism, the biological assumptions defining expected allele counts may be different for different loci. For example, as illustrated in FIG. 6, some chromosomes may possess some but not other polymorphic loci.

To allow for consideration of multiple loci, the process flow depicted in FIG. 10 includes a decision operation 1017, which determines whether any more loci need to be considered. If they do, the process reverts to process operation 1005 where genotype zygosity assumptions are provided for the next locus of the polyploid genome (or the next genomic locus of the polyploid organism). Thereafter, the model generation proceeds as described above, but with the new locus under consideration. Ultimately, all the loci of relevance for genotyping the organism are considered and modeled, and the process is finished as illustrated at 1019. Although the operations for building different models for different loci are illustrated as serial iterations in the FIG. 10, in some implementations, multiple processes for building one or more of the different models may be performed in parallel to speed up the processes.

Typically, the apparatus and process conditions employed to capture test data for genotyping a polyploid sample is also used to generate the training set data. And typically the polyploid organisms to be genotyped are of the same species as those used to generate the training set samples, with the same expected range of genotypes. In certain embodiments, a training set grows or otherwise changes with the addition of new members, such as those obtained from test samples during genotyping. Modified training sets can be used to periodically update the cluster model by parameter fitting and/or cluster center adjusting as described above.

The training set used to fit the parameters of the signal intensity functions may be used to adjust the cluster centers using a Bayesian method. In other embodiments, separate or overlapping but not identical data sets are used to (i) fit the parameters and (ii) adjust the clusters.

Cluster Locations—Parameter Fitting

The polyploid genotyping software implements a generic clustering model that can be adapted to cluster either allopolyploid or autopolyploid data. In some implementations, this model is based on an underlying measured signal (e.g., intensity) model of the assay. In this approach, the model assumes that for a given intensity channel the observed intensity is a function of the copy count of the allele associated with that channel. Various functions may be employed. In certain embodiments, the function is assumed to be non-linear and others it is assumed to be linear. Non-linear functions may employ only a single independent variable, which is the allele count for the channel, or may employ more than one independent variable, in which case at least one such variable is allele count. Non-linear functions may have an exponential component, in which allele count is raised to a power. One example of a general form of an intensity versus allele count function is given by:

$$\text{intensity}_a = x^*(\text{counts}_{\text{allele } a})^y + z$$

where x, y, and z are adjustable parameters of the model. A similar expression is used for the other channel, the b channel, for the second allele at the locus. The allele count may be represented as an integer value, although this is not necessary, as long at the relative quantities of the two alleles at a locus are correctly represented in the two intensity functions for the locus.

In an alternative embodiment, the general form of the intensity versus allele count function is given by:

$$\text{intensity}_a = x^* \ln(\text{counts}_{\text{allele } a}) + y$$

where x and y are adjustable parameters of the model.

Since the allele counts for a given genotype are known, two-dimensional cluster positions can be determined using the signal intensity expressions for both channels for a given genotype. The parameter values for x, y, and z in both the a and b channels are separately chosen based on the expected genotypes and the training set data. In certain embodiments, y is assumed to be equal for both the a and b channels. The challenge is then to identify the model parameter values that maximize the fit of the model to the data. In certain embodiments, the parameter values are fit via a pattern search with multiple different initialization conditions. This permits exploration of a wide range of parameter space with reduced risk of converging in local maximum that is quite unfavorable compared to a global maximum.

Depending upon the form of the model, various techniques may be employed to fit the model parameters to training set data. Certain techniques treat the data as a mixture of distributions, which are the clusters. In certain embodiments, the fitting procedure assumes that the mathematical form of the model will be a mixture of Gaussian distributions, and based on this finds a mean and a standard deviation for each Gaussian. To do this, the procedure employs the mentioned constraints (e.g., the number of polyploid genotypes, the form of the functions for signal intensity measurements, etc.). The technique converges after a few iterations of refining the estimates of the means, standard deviations, and the proportions of data points in each cluster. The result is a model that fits the training data reasonably well.

One fitting technique for mixture models is a maximum likelihood estimation, which may employ a well-known algorithm such as an expectation maximization (EM) algorithm, of which an example is described in Dempster, A. P., Laird, N. M., and Rubin D. B., "Maximum Likelihood from Incomplete Data via the EM Algorithm," Journal of the Royal Statistical Society B, 1977 [39]: 1-38, and in McLachlan, Geoffrey J., and T. Krishnan (1997), *The EM algorithm and extensions*, John Wiley and Sons. Both of these references are incorporated herein by reference for all purposes. Other maximization techniques may be employed. In addition other estimation techniques can be used, such as classical constrained maximum likelihood, MiniMax estimation, and Bayesian modelling with estimation using Gibbs sampling. If distributions other than Gaussian are modelled, an algorithm other than EM may be better suited.

In certain embodiments, the model generation process is not designed to fit all possible genotypes for an organism. This may be the case, when underlying biology suggests that not all possible genotypes (zygosities) will occur at a given locus. See FIG. 6 as an example. In an allotetraploid species, for example, the biology may suggest the occurrence of only three clusters based on the segregation of the alleles. See FIG. 5. Therefore, the model fitting process may have a notion of "active" clusters. This is an indication of which genotype clusters, out of all potential genotype clusters assuming maximum diversity in the organism, should actually occur in the samples under consideration. Genotypes that are not "active" are ignored in the optimization process. In allopolyploid clustering, the model generation process may iterate over different possible configurations of active clusters. This is also useful in various contexts such as in in-bred populations. For in-bred populations, the biology may suggest observations of only the homozygous genotype clusters. In such cases, the homozygous clusters can be identified as "active" and the model fitting process can proceed in fashion described herein.

Cluster Location Adjustment

In certain embodiments, the final version of a polyploid genotyping model employs the cluster positions using the model parameters identified as described. However, in some cases, this results in cluster positions that are not fully optimized to the actual positions of the samples. For example, the cluster positions may be underfit for available data in a cluster; as some clusters may have relatively many members (training set points) and the fitting process does not fully account for all of them. The cluster locations obtained from the intensity model are restrained by the nature and form of the model. In certain embodiments, the disclosed process may adjust the cluster positions to more closely match the observed sample data. This adjustment allows a cluster location to be moved from a model predicted location to new location not entirely constrained by the form of the model. In some implementations, this adjustment may take into account the amount and values of sample data. When only a single sample disagrees with the cluster position predicted by the model, the method may make a small adjustment to the cluster position. When many samples disagree, then the method makes a larger model adjustment. In some implementations, A Bayesian method may be used perform this update, which involves using the cluster locations predicted by the intensity model as prior, and obtaining the posterior from the prior and information of the sample data. The information of the sample data may include the number, the central tendency (median), and the distribution (e.g., median absolute deviation). In some implementations, the normal-gamma distribution (conjugate prior of normal distribution with unknown mean and variance) may be used to calculate the updated positions. The parametric model may be used to set the prior expectation, while the mode of the posterior distribution may be used to set the updated cluster positions. This same update methodology may be used to set the intensity (i.e., R value) for each genotyping cluster.

In certain embodiments, the overall process employing an adjustment in the cluster positions may be represented as follows:

1. For each active cluster, generated expected R and $\theta$ values (from the parameter fit method), where a. $\theta = \text{atan 2}(\text{intensity}_a, \text{intensity}_b)/(\pi/2)$ b. $R_{original} = \text{intensity}_a + \text{intensity}_b$ 2. The R values calculated above may be unscaled, so they can be scaled to the observed data as follows:
    a. For each sample
        i. Assign the sample to a cluster based on the value of $\theta$
        ii. Calculate the log ratio $\log(R_{sample}/R_{original})$
    b. Calculate the scaling estimate as the median log ratio across all samples
    c. Scale the R values for the clusters as $R_{updated} = R_{original} * e^{(scaling\ estimate)}$ 3. The next step is to update the "prior" location of the cluster specified by the model by incorporating information from the observed samples using the Normal-gamma distribution. The normal-gamma distribution describes the probability distribution of the parameters of a normal distribution with unknown mean and variance.

Normal-gamma distribution can be described as follows.

$(X,T) \sim \text{NormalGamma}(\mu, \lambda, \alpha, \beta)$

X: mean of unknown distribution

T: precision of unknown distribution $\mu$: prior estimate of mean $\lambda$: Number of psuedo-counts (i.e., weight) for the prior estimate of the mean $\alpha$: Weight for prior estimate of the variance $\beta$: Related to the prior estimate of variance After observation of n data points with sample mean x and sample variance s, the posterior probability distribution is given as $$P(\tau, \mu \mid X) =$$

$$NormalGamma\left(\frac{\lambda_0\mu_0 + n\bar{x}}{\lambda_0 + n}, \lambda_0 + n, \alpha_0 + \frac{n}{2}, \beta_0 + \frac{1}{2}\left(ns + \frac{\lambda_0 n(\bar{x} - \mu_0)^2}{\lambda_0 + n}\right)\right)$$

Using the parameters from the posterior probability distribution, the updated expectation of X is $\mu$, while the expectation of T is $\alpha*\beta^{-1}$.

a. For each cluster, assume the following prior values for the Normal-Gamma distribution
  i. For estimation of $\theta$
    1. $\mu$: From 1a above
    2. $\lambda$: 5
    3. $\alpha$: 5
    4. $\beta$: (constant related to ploidy)$^2$
  ii. For estimation of R
    1. $\mu$: From 2c above
    2. $\lambda$: 5
    3. $\alpha$: 5
    4. $\beta$: (0.1*0.1)
b. For estimation of both R and theta, use the following values for the observed data points
  i. n: Number of samples assigned to cluster
  ii. x: Median value of samples assigned to cluster
  iii. s: (1.4826*(Median absolute deviation of samples assigned to cluster))$^2$

Genotyping Polyploid Organisms

Cluster models such as those produced in accordance with the above description may be used in various ways to genotype one or more loci of a polyploid organism. Such techniques involve determining the cluster, which represents a particular genotype for a given locus, which is nearest to the sample data point under consideration. In certain embodiments, the nearness of a sample data point to a cluster position is determined by calculating a Euclidean distance. Other techniques known to those of skill in the art may be employed in appropriate circumstances. In addition to determining a nearest cluster, and hence assigning a locus genotype, the cluster assignment may be given a score indicating the reliability of the assignment. The reliability can be based on various criteria such as the specificity of the assignment based on, for example, whether the two nearest cluster positions are of nearly equal distances from the sample signal value.

Figure 11:
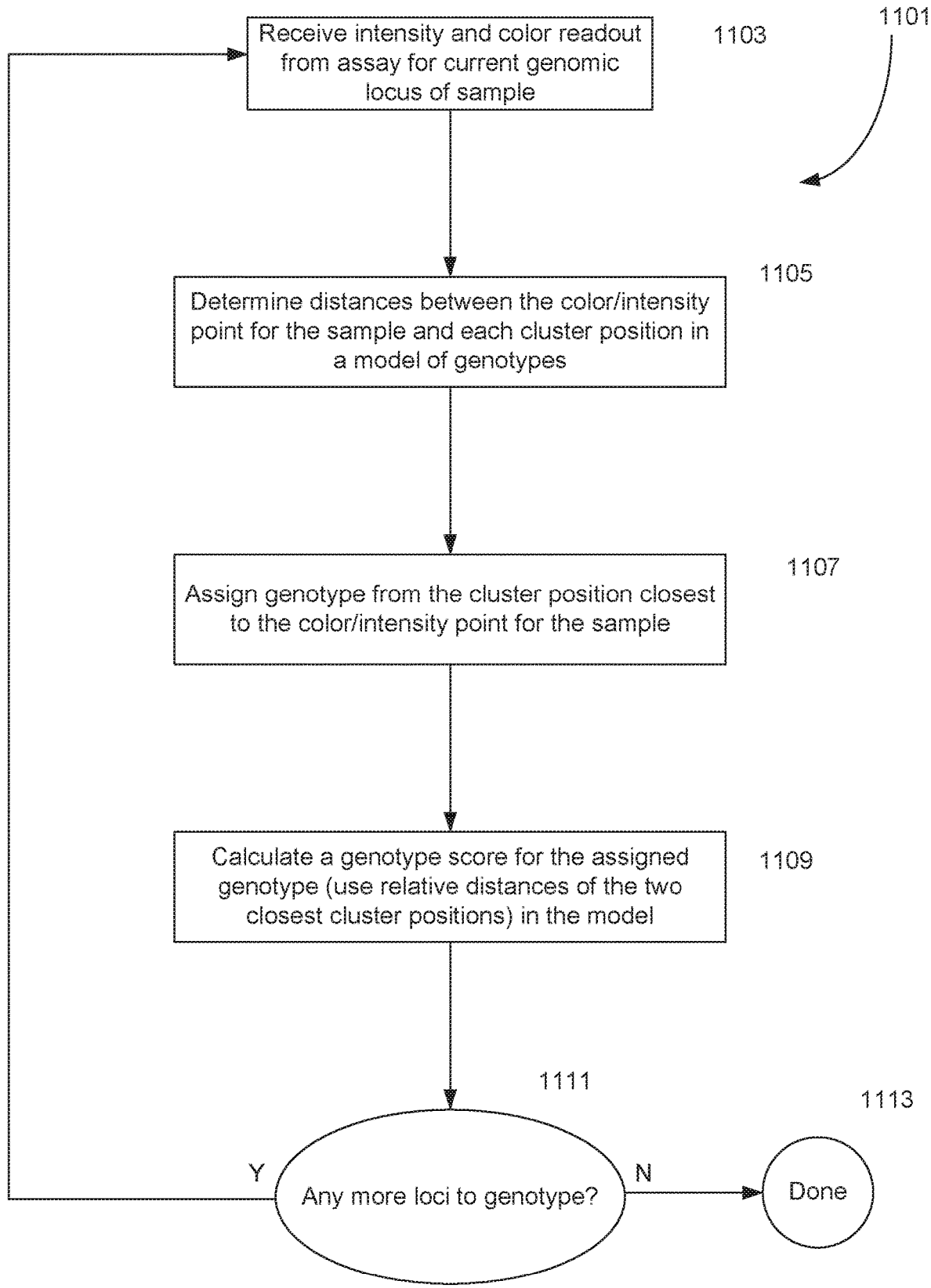
FIG. 11 presents a process flow for assigning a genotype to a sample locus and scoring the assignment.

An example of a process flow for assigning a genotype to a sample locus and scoring the assignment is depicted in the flowchart of FIG. 11. As shown, the process 1101 begins by receiving intensity and color readout data (or other signal strength versus nucleotide species data) from an assay for a current locus of the sample. See process operation 1103. Next, the genotyping system determines distances between the signal value for the current locus of the sample and each cluster position in a model of genotypes. See operation 1105. The distances may be determined using any suitable distance function such as, for example, Euclidean distances and inverse probabilities. As mentioned, such model may be a cluster model prepared as described above.

As an example, the genotyping method assigns a genotype by calculating the distance to the sample using the following expression for Euclidean distance:

$$\text{distance} = \sqrt{((\theta - \mu_\theta)/\sigma_\theta)^2 + ((R - \mu_R)/\sigma_R)^2}$$

where $\theta$ (theta) and R are the genotyping intensity coordinates for the sample.

After determining the distances between the signal value for the sample under consideration and each of the cluster positions, the genotyping system next assigns a genotype based on the genotype associated with the cluster position closest to the signal value obtained for the sample. This may be a matter of simply assigning the genotype for the cluster having the smallest Euclidean distance to the signal data for the sample in question. See process operation 1107.

Next, the genotyping system determines or calculates a genotype score for the assigned genotype. As explained, score may indicate the relative reliability of the genotype call. See operation 1109. In certain embodiments, the score is high for cases where the signal value for the sample is near to the closest cluster position but far away from the second closest cluster position. Conversely, the score may be low where the sample signal value is nearly equally close to the first and second closest cluster positions.

An example sequence for calculating a score proceeds as follows.

Across all clusters (each representing a distinct genotype), determine the minimum distance from the current sample's intensity values to each genotype Determine the genotype with the smallest distance and the genotype with the second smallest distance If there is no second genotype, or the distance to the second genotype is greater than the outlier threshold (e.g., about 4), then assume the second lowest distance is equal to the threshold distance.

Calculate the final score as a function of the relative distances to the first and second genotype clusters, e.g.:

$$\text{score} = 2*\left(1 - \frac{\text{distance}_{min}}{\text{distance}_{min} + \min(\text{distance}_{second\,min}, \text{distance}_{outlier})}\right) - 1$$

After determining the genotype assignment and assignment score for the current locus, the process may consider whether there are any further loci from the sample to genotype. See decision operation 1111. If so, the process returns to process operation 1103 where it receives signal data for the next genomic locus under consideration. Thereafter, the process proceeds through operations 1105, 1107, and 1109 as described above. When all loci of the polyploid sample under consideration are considered, the genotyping process is completed as indicated at 1113. The method illustrated here assigns genotypes and scores for different loci in serial iterations. However, in other implementations, multiple assignments for multiple loci may be performed in parallel.

Apparatus and Systems for Genotyping Samples

Samples and Sample Processing

Samples that are used for determining a genotype, e.g., a polyploid genotype at one or more loci of a polyploid genome, can include samples taken from any cell, tissue, or organ in which a genotype is to be determined. Typically, the samples contain nucleic acids that are that are present in cells.

The sample comprising the nucleic acid(s) to which the methods described herein are applied typically comprises a biological sample ("test sample"). In some embodiments, the nucleic acid(s) to be genotyped is purified or isolated by any of a number of well-known methods.

Accordingly, in certain embodiments the sample comprises or consists of a purified or isolated polynucleotide, or it can comprise samples such as a tissue sample, a biological fluid sample, a cell sample, and the like. In certain embodiments, the sample is a mixture of two or more biological samples, e.g., a biological sample can comprise two or more of a biological fluid sample, a tissue sample, and a cell culture sample.

In certain embodiments, samples can be obtained from sources, including, but not limited to, samples from different individuals, samples from different developmental stages of the same or different individuals, samples from different diseased individuals (e.g., individuals with cancer or suspected of having a genetic disorder), normal individuals, samples obtained at different stages of a disease in an individual, samples obtained from an individual subjected to different treatments for a disease, samples from individuals subjected to different environmental factors, samples from individuals with predisposition to a pathology, samples individuals with exposure to an infectious disease agent, and the like.

In certain embodiments samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue and/or cells.

Methods of isolating nucleic acids from biological sources are well known and will differ depending upon the nature of the source. One of skill in the art can readily isolate nucleic acid(s) from a source as needed for the method described herein. In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing.

Apparatus and Systems for Genotyping Polyploid Organisms

Analysis of the genetic data (e.g., hybridization data from a microarray and/or massively parallel sequencing data) and the genotyping are typically performed using various computer executed algorithms and programs. Therefore, certain embodiments employ processes involving data stored in or transferred through one or more computer systems or other processing systems. Embodiments disclosed herein also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In various embodiments, the data or information employed in the disclosed methods and apparatus is provided in an electronic format. Such data or information may include signal intensities for each of multiple channels of a sequencer or microarray configured to distinguish between distinct alleles or nucleotide types present a nucleic acid test sample, counts or densities of such alleles, reference sequences (including reference sequences providing solely or primarily polymorphisms), calls such as genotype calls at certain loci, genotype scores, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

One embodiment provides a computer program product and/or associated system for generating an output indicating the genotype at one or more loci in a polyploid test sample. One embodiment provides a computer program product and/or associated system for generating a cluster model to genotype at one or more loci in a polyploid test sample. The computer product may contain instructions for performing any one or more of the above-described methods for determining a genotype or generating a cluster model. As explained, the computer product may include a non-transitory and/or tangible computer readable medium having a computer executable or compilable logic (e.g., instructions) recorded thereon for enabling a processor to determine appropriate cluster positions for a model and/or genotype a test sample. In one example, the computer product includes a computer readable medium having a computer executable or compilable logic (e.g., instructions) recorded thereon for enabling a processor to generate a cluster model by: (a) identifying a plurality of active genotypes expected to be observed at a genomic locus in the polyploid organisms; (b) fitting a plurality of parameters of a first function relating a first signal magnitude produced in a microarray by a first nucleotide type present in a first allele at the genomic locus to a count of the first nucleotide type at the genomic locus, wherein fitting the plurality of parameters of the first function assumes the identified plurality of active genotypes are observed in the polyploid organisms; (c) fitting a plurality of parameters of a second function relating a second signal magnitude produced in the microarray by a second nucleotide type present in a second allele at the genomic locus to a count of the second nucleotide type at the genomic locus, wherein fitting the plurality of parameters of the second function assumes the identified plurality of active genotypes are observed in the polyploid organisms, wherein fitting the plurality of parameters to the first and second functions is performed using a training set of the first and second signal magnitudes obtained by assaying the genomic locus of a plurality of polyploid organisms, and wherein the first and second functions together identify cluster positions for genotypes at the genomic locus; and (d) adjusting the cluster positions identified by the first and second functions to more closely match observed data from the training set.

In some implementations, the computer product includes a computer readable medium having a computer executable or compilable logic (e.g., instructions) recorded thereon for enabling a processor to generate a cluster model by: fitting a plurality of parameters of a first function relating a first signal magnitude produced in a microarray by a first nucleotide type present in a first allele at a genomic locus of the polyploid organisms to a count of the first nucleotide type at the genomic locus; fitting a plurality of parameters of a second function relating a second signal magnitude produced in the microarray by a second nucleotide type present in a second allele at the genomic locus to a count of the second nucleotide type at the genomic locus; wherein fitting the plurality of parameters to the first and second functions is performed using a training set of the first and second signal magnitudes obtained by assaying the genomic locus for a plurality of organisms, and wherein the first and second functions together identify cluster positions for genotypes at the genomic locus; and adjusting the cluster positions identified by the first and second functions to more closely match observed data from the training set.

In some implementations, the computer product includes a computer readable medium having a computer executable or compilable logic (e.g., instructions) recorded thereon for enabling a processor to generate a cluster model by: identifying a plurality of active genotypes expected to be observed at a genomic locus of the polyploid organisms; fitting a plurality of parameters of a first function relating a first signal magnitude produced in a microarray by a first nucleotide type present in a first allele at the genomic locus to a count of the first nucleotide type at the genomic locus, wherein fitting the plurality of parameters of the first function assumes the identified plurality of active genotypes are observed in the polyploid genome; and fitting a plurality of parameters of a second function relating a second signal magnitude produced in the microarray by a second nucleotide type present in a second allele at the genomic locus to a count of the second nucleotide type at the genomic locus, wherein fitting the plurality of parameters of the second function assumes the identified plurality of active genotypes are observed in the polyploid genome; wherein fitting the plurality of parameters to the first and second functions is performed using a training set of the first and second signal magnitudes obtained by assaying the genomic locus for a plurality of organisms, an wherein the first and second functions together identify cluster positions for genotypes at the genomic locus.

The signal composition from a microarray or sequencer for a sample under consideration may be analyzed to determine magnitude (e.g., intensity) and color or other feature associated with relative quantities of alleles. This information then be used in cluster analysis and/or genotyping. In various embodiments, the cluster positions, function parameters, sample locations, genotypes, or combinations of these are stored in a database such as a relational or object database.

It should be understood that it is not practical, or even possible in most cases, for an unaided human being to perform the computational operations of the methods disclosed herein. For example, fitting parameter values to training data, adjusting cluster positions using a Bayesian method, and/or genotyping test samples using microarray data might require years of effort without the assistance of a computational apparatus.

The methods disclosed herein can be performed using a system for genotyping one or more loci of interest in a test sample. The system may include: (a) a sequencer or microarray for receiving nucleic acids from the test sample providing nucleic acid sequence information from the sample; (b) a processor; and (c) one or more computer-readable storage media having stored thereon instructions for execution on said processor to carry out a method for genotyping the one or more loci using a cluster model produced as described herein.

In some embodiments, the instructions may further include automatically recording information pertinent to the method such as genotype assignments and genotype scores. Further, based on the results of the processor-implemented analysis, the method may further involve prescribing, initiating, and/or altering treatment of a polyploid subject from whom the test sample was taken. This may involve performing one or more additional tests or analyses on additional samples taken from the organism.

Sequence or hybridization data (e.g., signal intensity and color) can be input into a computer or stored on a computer readable medium either directly or indirectly. In one embodiment, a computer system is directly coupled to a microarray or sequencing device that analyzes sequences of nucleic acids from samples. Signal intensities or other information from such tools are provided via interface in the computer system. Alternatively, the signals processed by system are provided from a storage source such as a database or other repository. Once available to the processing apparatus, a memory device or mass storage device buffers or stores, at least temporarily, signal information from the test nucleic acids. In addition, the memory device may store cluster information and/or genotypes for various chromosomes or genomes, etc. The memory may also store various routines and/or programs for analyzing the presenting the cluster model and/or called genotypes. Such programs/routines may include programs for performing statistical analyses, etc.

In one example, a user provides a sample into a microarray apparatus. Data is collected and/or analyzed by the apparatus which is connected to a computer. Software on the computer allows for data collection and/or analysis. Data can be stored, displayed (via a monitor or other similar device), and/or sent to another location. The computer may be connected to the internet which is used to transmit data to a handheld device utilized by a remote user (e.g., scientist or analyst). It is understood that the data can be stored and/or analyzed prior to transmittal. In some embodiments, raw data is collected and sent to a remote user or apparatus that will analyze and/or store the data. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to a building, city, state, country or continent.

In some embodiments, the methods also include collecting data regarding a plurality of polynucleotide sequences and sending the data to a computer or other computational system. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet. At the remote location various operations can be performed on the transmitted data as described below.

Among the types of electronically formatted data that may be stored, transmitted, analyzed, and/or manipulated in systems, apparatus, and methods disclosed herein are the following:
Intensity and color information obtained from a microarray
Intensity versus allele count parameters and/or functions
Cluster positions in a cluster model
Reads obtained by sequencing nucleic acids in a test sample
Tags obtained by aligning reads to a reference genome or other reference sequence or sequences
A reference genome or sequence
Thresholds for calling genotypes of loci
The actual genotype calls at particular loci
Diagnoses (clinical condition associated with the calls)
Recommendations for further tests derived from the calls and/or diagnoses
Treatment and/or monitoring plans derived from the calls and/or diagnoses These various types of data may be obtained, stored transmitted, analyzed, and/or manipulated at one or more locations using distinct apparatus. The processing options span a wide spectrum. At one end of the spectrum, all or much of this information is stored and used at the location where the test sample is processed, e.g., a research facility or other clinical setting. In other extreme, the sample is obtained at one location, it is processed and optionally hybridized or sequenced at a different location, genotype calls are made at one or more different locations, and diagnoses, recommendations and/or plans are prepared at still another location (which may be a location where the sample was obtained).

In various embodiments, the signals are generated with the microarray or sequencing apparatus and then transmitted to a remote site where they are processed to produce genotype calls. At this remote location, as an example, microarray signal information is applied a cluster model for polyploid genotyping. Also at the remote location, the signal information is converted to genotypes and genotype scores.

Among the processing operations that may be employed at distinct locations are the following:
Sample collection
Sample processing preliminary to sequencing
Sequencing/hybridization with a microarray
Analyzing signal data deriving genotypes at one or more loci
Diagnosis or research conclusion
Reporting a diagnosis and/or research conclusion
Developing a plan for further treatment, testing, and/or monitoring
Executing the plan Any one or more of these operations may be automated. Typically, the microarray signal analysis and genotype calling will be performed computationally. The other operations may be performed manually or automatically.

Examples of locations where sample collection and/or processing may be performed include research facilities and field locations (where a sample collection tool or kit is provided). Examples of locations where sequencing may be performed include research facilities, field locations, health practitioners' offices, clinics, patients' homes (where a sample sequencing apparatus and/or kit is provided), etc. In some embodiments, the sample collection, sample processing, and sequencing operations are performed at a first location and the analyzing and genotyping operation is performed at a second location. However, in some cases, the sample collection is collected at one location (e.g., field site) and the sample processing and sequencing is performed at a different location that is optionally the same location where the analyzing and deriving take place. The location where the sequencing takes place may be provided with a dedicated network connection for transmitting sequence data (typically reads) in an electronic format. Such connection may be wired or wireless and have and may be configured to send the data to a site where the data can be processed and/or aggregated prior to transmission to a processing site.

The analyzing and/or deriving operations may be performed at any of the foregoing locations or alternatively at a further remote site dedicated to computation and/or the service of analyzing nucleic acid sequence data. Such locations include for example, clusters such as general purpose server farms, the facilities of a genotype analysis service business, and the like. In some embodiments, the computational apparatus employed to perform the analysis is leased or rented. The computational resources may be part of an Internet accessible collection of processors such as processing resources colloquially known as the cloud. In some cases, the computations are performed by a parallel or massively parallel group of processors that are affiliated or unaffiliated with one another. The processing may be accomplished using distributed processing such as cluster computing, grid computing, and the like. In such embodiments, a cluster or grid of computational resources collective form a super virtual computer composed of multiple processors or computers acting together to perform the analysis and/or derivation described herein. These technologies as well as more conventional supercomputers may be employed to process sequence data as described herein. Each is a form of parallel computing that relies on processors or computers. In the case of grid computing these processors (often whole computers) are connected by a network (private, public, or the Internet) by a conventional network protocol such as Ethernet. By contrast, a supercomputer has many processors connected by a local high-speed computer bus.

In various embodiments, a sequence of the above-listed operations may be triggered by a user or entity initiating sample collection, sample processing and/or sequencing. After one or more these operations have begun execution the other operations may naturally follow. For example, the sequencing operation may cause microarray signal to be automatically collected and sent to a processing apparatus which then conducts, often automatically and possibly without further user intervention, the genotyping operation. In some implementations, the result of this processing operation is then automatically delivered, possibly with reformatting, to a system component or entity that processes reports. This is accomplished even though parts of the overall system are physically separated and possibly remote from the location of, e.g., the sample and sequence/microarray apparatus.

Figure 12:
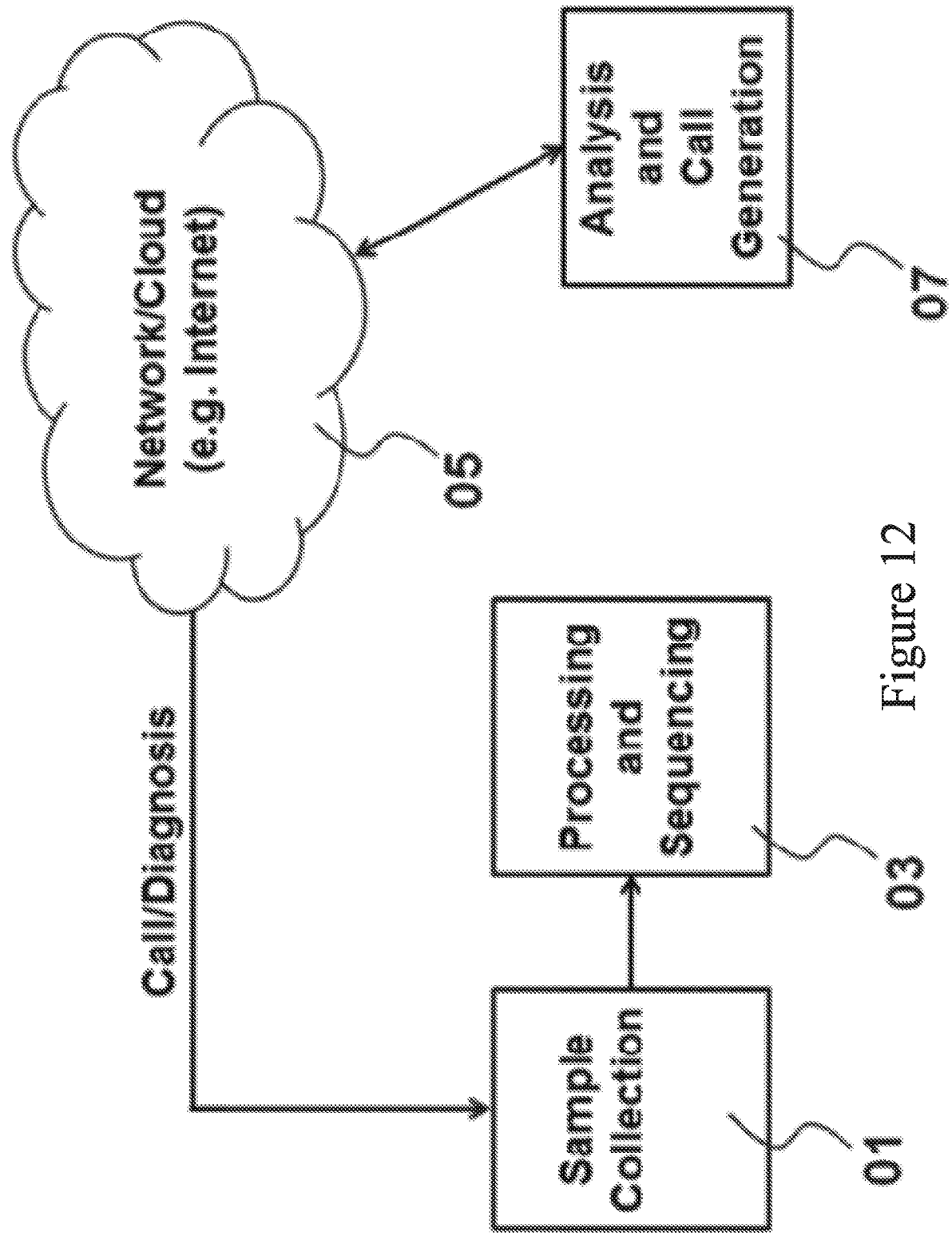
FIG. 12 shows one implementation of a dispersed system for producing a genotype call of a test sample.

FIG. 12 shows one implementation of a dispersed system for producing a genotype call of a test sample. A sample collection location 01 is used for obtaining a test sample. The samples then provided to a processing and sequencing location 03 where the test sample may be processed and sequenced as described above. Location 03 includes apparatus for processing the sample as well as apparatus for sequencing/hybridization of the processed sample. The result of the sequencing, as described elsewhere herein, is microarray signal data which is typically provided in an electronic format and provided to a network such as the Internet, which is indicated by reference number 05 in FIG. 12.

The microarray signal data is provided to a remote location 07 where analysis and call generation are performed. This location may include one or more powerful computational devices such as computers or processors. After the computational resources at location 07 have completed their analysis and generated a genotype call from the information received, the call is relayed back to the network 05. In some implementations, not only is a call generated at location 07 but an associated diagnosis is also generated. The call and/or score are then transmitted across the network and back to the sample collection location 01 as illustrated in FIG. 12. As explained, this is simply one of many variations on how the various operations associated with generating a call or diagnosis may be divided among various locations. One common variant involves providing sample collection and processing and sequencing in a single location. Another variation involves providing processing and sequencing at the same location as analysis and call generation.

EXAMPLES

Example 1: Sample Processing and Data Generation

Various implementation of the disclosure may be implemented using microarray platforms. The methods and systems disclosed herein can be useful for whole-genome genotyping. This example provides a workflow for using microarray platform to process samples, generate data, and analyze the data for clustering data and genotyping samples.

Figure 13:
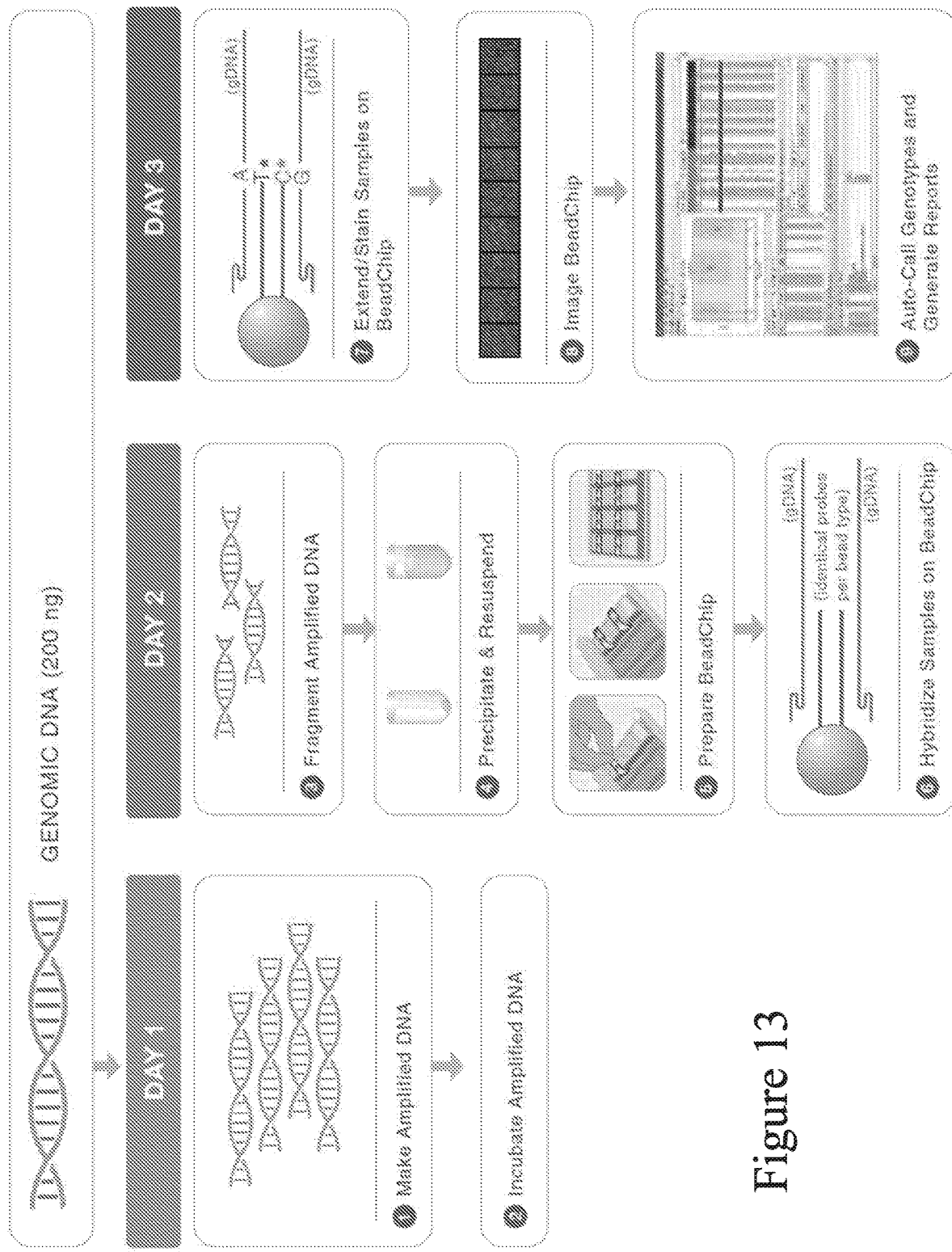
FIG. 13 illustrates an example workflow implemented on the Illumina Infinium™ platform.

In this example, the Illumina Infinium™ protocol is described and summarized in FIG. 13. The workflow begins with an overnight amplification of the DNA sample. This amplification has no appreciable allelic partiality. A relatively low DNA sample requirement of 200 ng is sufficient to assay over 300,000 SNP loci. The DNA samples are denatured and neutralized to prepare them for amplification. The amplified product is end fragmented. The denatured DNA is isothermally amplified in an overnight step. Whole genome amplification uniformly increases the amount of the DNA sample by several thousand sold without using large amount of amplification biases. (Steps 1 and 2)

The amplified product is fragmented by a process that does not require gel electrophoresis. The process uses endpoint fragmentation to avoid over fragmenting the sample. (Step 3).

After isopropanol precipitation, the fragmented DNA is collected by centrifugation. The precipitated DNA is then resuspended in hybridization buffer. (Step 4).

The beast chip is prepared for hybridization in the capillary flow-through chamber. Samples are applied to the bead chip. The loaded chip is incubated overnight. (Step 5)

The DNA samples are then hybridized to locus specific 50-mers covalently linked to one of over 300,000 bead types in the overnight hybridization step. Each bead has hundreds of thousands of locus specific oligomers targeting the same SNP. One bead type corresponds to each allele for SNP locus. (Step 6)

After hybridization, allelic specificity is conferred by enzymatic base extension. Because the different bead types include allele specific probes, the specificity can be determined when growing the 50-mers using the captured DNA fragments including the allele of interest. Products are subsequently fluorescently stained. Two different colors, e.g., red and green, are used to stain two different nucleotides corresponding to the two alleles. (Step 7)

The intensities of red and green fluorescence are detected by a scanning device such as the iScan system (Step 8).

Intensity data of the red and green channels are analyzed using the methods described above to develop clusters and assign genotypes. (Step 9)

Typically, the apparatus and process conditions employed to capture test data for genotyping a polyploid sample is also used to generate the training set data. And typically the polyploid organisms to be genotyped are of the same species as those used to generate the training set samples, with the same expected range of genotypes. In certain embodiments, a training set grows or otherwise changes with the addition of new members, such as those obtained from test samples during genotyping. Modified training sets can be used to periodically update the cluster model by parameter fitting and/or cluster center adjusting as described above.

The training set used to fit the parameters of the signal intensity functions may be used to adjust the cluster centers using a Bayesian method. In other embodiments, separate or overlapping but not identical data sets are used to (i) fit the parameters and (ii) adjust the clusters.

What is claimed is:

1. A method of genotyping a genomic locus of a polyploid genome of a polyploid organism to be genotyped, the method comprising:
   providing a cluster model for genotyping polyploid organisms produced by:
   (a) identifying a plurality of active genotypes expected to be observed at the genomic locus in the polyploid organisms;
   (b) fitting a plurality of parameters of a first function relating a first signal magnitude produced in a microarray by a first nucleotide type present in a first allele at the genomic locus to a count of the first nucleotide type at the genomic locus, wherein fitting the plurality of parameters of the first function assumes the identified plurality of active genotypes are observed in the polyploid organisms;
   (c) fitting a plurality of parameters of a second function relating a second signal magnitude produced in the microarray by a second nucleotide type present in a second allele at the genomic locus to a count of the second nucleotide type at the genomic locus, wherein fitting the plurality of parameters of the second function assumes the identified plurality of active genotypes are observed in the polyploid organisms, wherein fitting the plurality of parameters to the first and second functions is performed using the first and second signal magnitudes obtained by assaying the genomic locus of a plurality of polyploid organisms of a training set, and wherein the first and second functions together identify cluster positions for genotypes at the genomic locus; and (d) adjusting the cluster positions identified by the first and second functions to more closely match observed data from the training set;

receiving a first signal magnitude produced in a microarray by the first nucleotide type at the genomic locus of the polyploid organism to be genotyped, and receiving a second signal magnitude produced in the microarray by the second nucleotide type at the genomic locus of the polyploid organism to be genotyped, wherein the first and second signal magnitudes together identify a two-dimensional position for a genotype of the genomic locus of the polyploid organism to be genotyped;

comparing the two-dimensional position to the cluster positions in the cluster model for the genomic locus; and assigning a genotype to the genomic locus of the polyploid organism to be genotyped based on a distance between the two-dimensional position and a nearest cluster position in the cluster model.

2. The method of claim 1, wherein identifying the plurality of active genotypes comprises identifying fewer than all possible combinations of the first and second nucleotide types at the genomic locus.

3. The method of claim 2, wherein the polyploid genome is an allopolyploid genome.

4. The method of claim 3, wherein the polyploid genome is an allotetraploid genome and at most three active genotypes are identified.

5. The method of claim 1, wherein at least one of the first and second functions has the form:

$$\text{intensity}_a = x^*(\text{counts}_{allele\ a})^y + z$$

wherein x, y, and z are adjustable parameters, $\text{intensity}_a$ is the first signal magnitude produced in the microarray, and $\text{counts}_{allele\ a}$ is the count of the first nucleotide type at the genomic locus.

6. The method of claim 1, wherein both the first and second function has the form:

$$\text{intensity}_a = x^*(\text{counts}_{allele\ a})^y + z$$

wherein x, y, and z are adjustable parameters, $\text{intensity}_a$ is the first signal magnitude produced in the microarray, and $\text{counts}_{allele\ a}$ is the count of the first nucleotide type at the genomic locus.

7. The method of claim 1, wherein at least one of the first and second functions is a non-linear function.

8. The method of claim 1, wherein fitting a plurality of parameters of the first and second functions in (b) and (c) comprises an unsupervised machine learning process.

9. The method of claim 1, wherein fitting a plurality of parameters of the first and second functions in (b) and (c) comprises a supervised machine learning process.

10. The method of claim 1, wherein fitting a plurality of parameters of at least one the first and second functions in (b) and (c) comprises a gradient method.

11. The method of claim 10, wherein the gradient method is a maximum likelihood estimation.

12. The method of claim 11, wherein the maximum likelihood estimation fits adjustable parameters to the training set data using a Gaussian definition of clusters in the training set.

13. The method of claim 12, wherein the maximum likelihood estimation fits the adjustable parameters to the training set data to produce a separate Gaussian definition of clusters for each of the plurality of active genotypes identified in (a).

14. The method of claim 1, wherein adjusting the cluster positions comprises updating the cluster positions using a Bayesian method.

15. The method of claim 14, wherein updating the cluster positions using a Bayesian method comprises: using the cluster positions identified by the first and second functions as prior, and obtaining posterior from the prior and the observed data of the training set.

16. The method of claim 15, wherein obtaining the posterior comprises obtaining the posterior from the prior and a number, a central tendency, and variance of the observed data of the training set.

17. A system for genotyping polyploid organisms, the system comprising:

a microarray configured to generate a first signal in response to contact with a first nucleotide type present in a first allele at a genomic locus of the polyploid organisms and generate a second signal in response to contact with a second nucleotide type present in a second allele at the genomic locus of the polyploid organisms; and one or more processors configured to (i) receive data representing magnitudes of the first and second signals produced in the microarray by the first and second nucleotide types at the genomic locus of a polyploid organism to be genotyped, wherein the first and second signal magnitudes together identify a two-dimensional position for a genotype of the genomic locus of the polyploid organism to be genotyped;

(ii) determine a plurality of cluster positions of a cluster model by:

(a) identifying a plurality of active genotypes expected to be observed at the genomic locus in the polyploid organisms;

(b) fitting a plurality of parameters of a first function relating the first signal magnitude to a count of the first nucleotide type at the genomic locus, wherein fitting the plurality of parameters of the first function assumes the identified plurality of active genotypes are observed in the polyploid organisms;

(c) fitting a plurality of parameters of a second function relating the second signal magnitude to a count of the second nucleotide type at the genomic locus, wherein fitting the plurality of parameters of the second function assumes the identified plurality of active genotypes are observed in the polyploid organisms, wherein fitting the plurality of parameters to the first and second functions is performed using the first and second signal magnitudes obtained by assaying the genomic locus of a plurality of polyploid organisms of a training set, and wherein the first and second functions together identify cluster positions for genotypes at the genomic locus; and (d) adjusting the cluster positions identified by the first and second functions to more closely match observed data from the training set;
(iii) compare the two-dimensional position for the genotype of the genomic locus of the polyploid organism to be genotyped to the cluster positions determined by the cluster model for the genomic locus; and
(iv) assign a genotype to the polyploid organism to be determined at the genomic locus based on a distance between the two-dimensional positions and a nearest cluster position in the cluster model.

18. The system of claim 17, wherein the one or processors are further configured to assign a score to the assigned genotype.

19. The system of claim 18, wherein the one or processors are further configured to assign the score by calculating the score from an expression using (i) the distance between the locus genotype of the polyploid genome and the nearest cluster position in the cluster model, and (ii) a distance between the locus genotype of the polyploid genome and a second nearest cluster position in the cluster model.

20. A computer program product comprising a non-transitory machine readable medium storing program code that, when executed by one or more processors of a computer system, causes the computer system to implement a method for genotyping a genomic locus of a polyploid genome of a polyploid organism to be genotyped, said program code comprising:
 code for providing a cluster model for genotyping polyploid organisms produced by:
  (a) identifying a plurality of active genotypes expected to be observed at the genomic locus in the polyploid organisms;
  (b) fitting a plurality of parameters of a first function relating a first signal magnitude produced in a microarray by a first nucleotide type present in a first allele at the genomic locus to a count of the first nucleotide type at the genomic locus, wherein fitting the plurality of parameters of the first function assumes the identified plurality of active genotypes are observed in the polyploid organisms;
  (c) fitting a plurality of parameters of a second function relating a second signal magnitude produced in the microarray by a second nucleotide type present in a second allele at the genomic locus to a count of the second nucleotide type at the genomic locus, wherein fitting the plurality of parameters of the second function assumes the identified plurality of active genotypes are observed in the polyploid organisms,
   wherein fitting the plurality of parameters to the first and second functions is performed using the first and second signal magnitudes obtained by assaying the genomic locus of a plurality of polyploid organisms of a training set, and
   wherein the first and second functions together identify cluster positions for genotypes at the genomic locus; and
  (d) adjusting the cluster positions identified by the first and second functions to more closely match observed data from the training set;
 code for receiving a first signal magnitude produced in a microarray by the first nucleotide type at the genomic locus of the polyploid organism to be genotyped, and receiving a second signal magnitude produced in the microarray by the second nucleotide type at the genomic locus of the polyploid organism to be genotyped, wherein the first and second signal magnitudes together identify a two-dimensional position for a genotype of the genomic locus of the polyploid organism to be genotyped;
 code for comparing the two-dimensional position to the cluster positions in the cluster model for the genomic locus; and
 code for assigning a genotype to the genomic locus of the polyploid organism to be genotyped based on a distance between the two-dimensional position and a nearest cluster position in the cluster model.

* * * * *

UNITED STATES PATENT AND TRADEMARK OFFICE
CERTIFICATE OF CORRECTION

| | | |
|---|---|---|
| PATENT NO. | : 11,456,055 B2 | Page 1 of 1 |
| APPLICATION NO. | : 16/305818 | |
| DATED | : September 27, 2022 | |
| INVENTOR(S) | : Ryan Kelley | |

It is certified that error appears in the above-identified patent and that said Letters Patent is hereby corrected as shown below:

In the Claims

1. In Line 1 of Claim 18 (Column 33, Line 13) change "one or processors" to --one or more processors--.

2. In Line 1 of Claim 19 (Column 33, Line 16) change "one or processors" to --one or more processors--.

Signed and Sealed this
Seventh Day of February, 2023

*Katherine Kelly Vidal*

Katherine Kelly Vidal
*Director of the United States Patent and Trademark Office*